United States Patent [19]

Willis et al.

[11] Patent Number: 5,189,053

[45] Date of Patent: Feb. 23, 1993

[54] IMIDAZOL(IN)E SUBSTITUTED HALOARYLPYRAZOLE PESTICIDES

[75] Inventors: Robert J. Willis, Fulbourn; Mary J. O'Mahony, Duxford; Bryan G. Roberts, Cambridge, all of England

[73] Assignee: Schering Agrochemicals Limited, England

[21] Appl. No.: 797,365

[22] Filed: Nov. 25, 1991

Related U.S. Application Data

[62] Division of Ser. No. 564,729, Aug. 8, 1990, Pat. No. 5,109,012.

[30] Foreign Application Priority Data

Aug. 10, 1989 [GB] United Kingdom ............... 8918314
Mar. 24, 1990 [GB] United Kingdom ............... 9006653

[51] Int. Cl.$^5$ .................... A01N 43/54; A01N 43/50; C07D 403/12; C07D 403/04
[52] U.S. Cl. .................... 514/397; 548/313.4; 548/314.4; 548/312.7
[58] Field of Search .................... 548/336; 514/397

[56] References Cited

U.S. PATENT DOCUMENTS 4,032,522 6/1977 Baldwin et al. ................... 548/336

OTHER PUBLICATIONS

Rufer et al, "Nitroimidazole derivatives" CA 84:4960V (1976).
Rufer et al, "Chemotherapeutic nitroheterocycles, etc" CA 26381j (1976).

Primary Examiner—Patricia L. Morris
Attorney, Agent, or Firm—Osterlenk, Faber, Gerb & Soffen

[57] ABSTRACT

Compounds of formula I

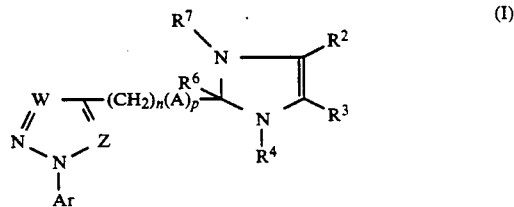

and salts thereof, in which Ar, W, Z, A, $R^{1-7}$, Y, m, p and n have the meanings given in the description, have pesticidal activity especially against insects, acarids and animal endoparasites.

17 Claims, No Drawings

IMIDAZOL(IN)E SUBSTITUTED HALOARYLPYRAZOLE PESTICIDES

This is a division of application Ser. No. 07/564,729, filed Aug. 8, 1990, now U.S. Pat. No. 5,109,012.

This invention relates to new compounds having pesticidal and especially insecticidal, acaricidal and animal endoparasiticidal activity.

In our EP 350 237, is disclosed pesticidal 2-aryl-triazoles which can carry a wide range of groups in the 4 and 5 positions, including aryl and heterocyclyl. The only examples of compounds having such substituents are those where the substituent is morpholino, pyrrolidino or piperidino and with these compounds the heterocycle is linked through its nitrogen atom to the triazole.

In U.S. Pat. Nos. 4,614,534, 4,740,231 and EP 205 023, there are disclosed 1-arylpyrazoles, which have activity as herbicides, and which can be substituted in the 4-position by a wide range of heterocycles. Amongst the heterocycles mentioned is imidazole, but except when it is an N-alkyl substituted imidazole, the imidazole is always nitrogen linked to the pyrazole. The heterocycles may be substituted by halogen, nitro, alkyl, alkoxy, alkylthio or haloalkyl. Of these three specifications, only one, U.S. Pat. No. 4,614,534, exemplifies compounds comprising an imidazole group, and in these compounds, the imidazole is unsubstituted and is nitrogen linked to the pyrazole.

In U.S. Pat. No. 4,740,231, the 5-position of the pyrazole is substituted by an amino group which itself is substituted with an oximinoethyl group. In this patent the substituent in the 4-position can also be a cyano or nitro group and the only Examples are to compounds of this type, ie no heterocyclyl substituted compounds are exemplified. As well as being herbicidal, the compounds are said to be insecticidal, although no details of such activity is given and there are no data to support this latter activity.

We have now found that certain aryl-1,2,3-triazoles and arylpyrazoles in which an imidazol(in)e group is attached directly or indirectly through its 2-position to the triazole or pyrazole ring, have unexpected pesticidal activity. Many of the compounds have systemic activity—eg when applied to an animal at a site remote from the site of the pest the compound will still act against the pest, eg sheep blowfly. Such activity is very unusual with totally synthetic insecticides. The compounds also show activity against animal endoparasites. This combination of insecticidal and endoparasitic activity is also uncommon and could not be predicted from the prior art.

The present invention thus provides a compound of formula I

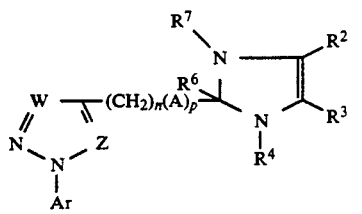

and salts thereof, in which
Ar is aryl;
W is N and Z is $CR^5$; or W is $CR^1$ and Z is N or $CR^5$;
A is $S(O)_m$, $-CH=CH-$, O or NH;
$R^1$ is hydrogen, optionally substituted alkyl, halogen or $R^{20}S(O)_q$;
$R^2$ and $R^3$ are hydrogen, alkyl, alkenyl or alkynyl, each of which is optionally substituted, aryl, heterocyclyl, cyano, halogen, nitro, $YR^{20}$, $S(O)_2NR^8R^9$, CHO and functional derivatives thereof, $NR^8R^9$ or $CYNR^8R^9$; either
(i) $R^4$ and $R^7$ which may be the same or different, are hydrogen, optionally substituted alkyl, optionally substituted alkenyl, acyl or optionally substituted alkoxycarbonyl, and $R^6$ is hydrogen, or
(ii) $R^4$ is as defined above and $R^6$ and $R^7$ form a bond or $R^7$ is as defined above and $R^4$ and $R^6$ form a bond;
$R^5$ is hydrogen, alkyl, optionally substituted amino or halogen;
$R^8$ and $R^9$ are the same or different and are hydrogen, optionally substituted alkyl, acyl or aryl, or together with the nitrogen to which they are attached, form a 5 to 7 membered ring which can contain other hetero atoms;
$R^{20}$ is optionally substituted alkyl;
Y is O or S;
m is 0, 1 or 2;
p is 0 or 1;
n is 0, 1 or 2; and
q is 0, 1 or 2, with the proviso that when W is $CR^1$ and Z is $CR^5$ and n and p are both 0, $R^4$ and $R^7$ are not alkyl.

Alkyl, alkoxy and alkylthio groups are preferably of 1 to 4 carbon atoms. Alkylthio groups are preferably methylthio. Alkenyl or alkynyl groups are generally of 2 to 5 carbon atoms. These groups may be substituted by one or more of the same or different groups such as halogen, $YR^{20}$, dihalocyclopropyl, cyano, nitro, optionally substituted amino, acyloxy and aryl. Aryl groups are usually phenyl, optionally substituted, e.g. by halogen, alkyl, haloalkyl, alkoxy, haloalkoxy, alkylthio, haloalkylthio, haloalkylsulphonyl, cyano or nitro. The term aryl may include heteroaryl groups such as imidazolyl, thienyl, furyl or pyridyl. The term "acyl" includes the residue of sulphonic and phosphorus containing acids as well as carboxylic acids. Acyl groups may be for example alkanoyl, e.g. of 1 to 4 carbon atoms, or alkylsulphonyl or haloalkylsulphonyl. Optionally substituted amino groups are generally of formula $NR^8R^9$. Heterocyclyl groups are generally 4 to 6 membered and can contain various hetero atoms, such as oxygen, nitrogen or sulphur.

When $R^8$ and $R^9$ form a ring this is generally a morpholino or piperidino ring. This ring can carry another fused ring and/or can be substituted, e.g. by one or more optionally substituted alkyl groups. Functional derivatives of CHO include oximes, hydrazones and semicarbazones.

A particularly preferred group of compounds are those where Ar is 2,6-dichloro-4-trifluoromethylphenyl or 2-nitro-4-trifluoromethylphenyl. It is generally preferred that W is $CR^1$, in which case $R^1$ is preferably hydrogen or alkyl. It is also preferred that $R^6$ and $R^7$ form a bond, in which case $R^4$ is preferably hydrogen. When W is $CR^1$ and Z is $CR^5$ and n and p are both 0, but also for all other compounds, it is preferred that at least one, and especially both, of $R^2$ and $R^3$ are cyano. n and p are preferably 0. $R^5$ is preferably halogen, especially chlorine.

The compounds of the invention have pesticidal activity and have insecticidal and/or acaricidal and/or animal endoparasiticidal activity.

They are particularly useful in combating a variety of economically important insects, and acarids including animal ectoparasites, e.g. Lepidoptera, including *Spodoptera littoralis, Heliothis armigera*, and *Pieris brassicae;* Diptera, including *Musca domestica, Ceratitis capitata, Erioischia brassicae, Lucilia sericata* and *Aedes aegypti;* Homoptera, including aphids such as *Megoura viciae* and *Nilaparvata lugens;* Coleoptera, including *Phaedon cochleariae, Anthonomus grandis* and corn rootworms (Diabrotica spp., eg. *Diabrotica undecimpunctata*); Orthoptera, including *Blattella germanica;* ticks, e.g. *Boophilus microplus* and lice, including *Damalinia bovis* and *Linognathus vituli.* Some compounds also have activity against plant parasitic nematodes, for example root-knot nematodes, such as Meloidogyne spp. and cyst forming nematodes, such as Heterodera spp..

The compounds of the invention are also active against animal and human endoparasites and especially helminths, ie nematodes, trematodes and cestodes, especially Trichostrongyloidea, eg *Haemonchus contortus,* Trichostrongylus spp; Dictyocaulus spp; Ascaridoidea, eg Toxocara spp; Strongylus spp; and Filarioidea, eg *Dirofilaria immitis,* Onchocerca spp: Trematoda, including *Fasciola hepatica* and Schistosoma spp.; and Cestoda, including Taenia spp and Moniezia spp., and protozoan parasites, eg Plasmodium spp.; Trypanosoma spp. and Eimeria spp..

As previously mentioned many of the compounds are active systemically, especially against animal ecto- and endoparasites.

The invention thus provides a method of combating pests, especially insects, acarids or animal endoparasites, at a locus or host for the pest, infested or liable to be infested therewith, which comprises applying to the locus, host and/or the pest, a compound of formula I, as defined above.

The invention also provides a pesticidal composition which comprises a compound of the invention in admixture with an agriculturally or veterinarily acceptable diluent or carrier.

The invention also provides a pharmaceutical composition which comprises a compound of the invention in admixture with an pharmaceutically acceptable diluent or carrier.

More than one compound of the invention can, of course, be included in the composition.

In addition the composition can comprise one or more additional pesticides, for example compounds known to possess herbicidal, fungicidal, insecticidal, acaricidal or nematicidal and other veterinary or pharmaceutical properties. Alternatively the compounds of the invention can be used in sequence with the other pesticides.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyne-4,7-diol, or ethoxylated acetylenic glycols. Examples of a cationic surface-active agent include, for instance, an aliphatic mono-, di-, or polyamine as an acetate, naphthenate or oleate; an oxygen-containing amine such a amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of insecticidal, acaricidal compounds, for example, a solution, a dispersion, an aqueous emulsion, a dusting powder, a seed dressing, a fumigant, a smoke, a dispersible powder, an emulsifiable concentrate, granules or baits; and when being used as an animal or human parasiticide, can be in the form of a preparation, eg for oral, parenteral or dermal application, eg in the form of powders, solutions, suspensions, tablets, capsules, drenches, boluses, pour-ons-, dips, sprays, injectables or as food additives. Moreover it can be in a suitable form for direct application or as a concentrate or primary composition which requires dilution with a suitable quantity of water or other diluent before application.

As a dispersion, the composition comprises a compound of the invention dispersed in a liquid medium, preferably water. It is often convenient to supply the consumer with a primary composition which can be diluted with water to form a dispersion having the desired concentration. The primary composition can be provided in any one of the following forms. It can be a dispersible solution which comprises a compound of the invention dissolved in a water-miscible solvent with the addition of a dispersing agent. A further alternative comprises a compound of the invention in the form of a finely ground powder in association with a dispersing agent and intimately mixed with water to give a paste or cream which can if desired be added to an emulsion of oil in water to give a dispersion of active ingredient in an aqueous oil emulsion.

An emulsifiable concentrate comprises a compound of the invention dissolved in a water-immiscible solvent together with an emulsifying agent and which is formed into an emulsion on mixing with water.

A dusting powder comprises a compound of the invention intimately mixed with a solid pulverulent diluent, for example, kaolin.

A granular solid comprises a compound of the invention associated with similar diluents to those which may be employed in dusting powders, but the mixture is granulated by known methods. Alternatively it comprises the active ingredient adsorbed or absorbed on a pre-granular diluent, for example, Fuller's earth, attapulgite or limestone grit.

A wettable powder usually comprises the active ingredient in admixture with a suitable surfactant and an inert powder diluent such as china clay.

Another suitable concentrate, particularly when the product is a solid, is a flowable suspension concentrate which is formed by grinding the compound with water, a wetting agent and a suspending agent.

Baits can include an attractant and may comprise a protein hydrolysate e.g. for the control of fruit flies, sugar e.g. for the control of adult Musca spp or corn cob e.g. for the control of cockroaches.

The concentration of the active ingredient in the composition of the present invention is preferably within the range of 1 to 30 per cent by weight, especially 5 to 30 per cent by weight. In a primary composition the amount of active ingredient can vary widely and can be, for example, from 5 to 95 per cent by weight of the composition.

The compounds of the invention may be prepared by a variety of methods known in the art.

For example: a compound of formula II

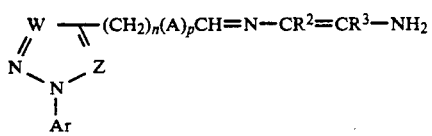
(II)

where p is 0, or p is 1 and A is —CH=CH—, is ring closed to give a compound of formula I, where $R^4$ is hydrogen, and p is 0, or p is 1 and A is —CH=CH—, and $R^6$ and $R^7$ form a bond, and optionally modifying this in known manner to give compounds where $R^4$ is other than hydrogen. Suitable reagents for ring closure include N-chlorosuccinimide and 2,3-dichloro-5,6-dicyano-1,4-benzoquinone.

The compound of formula II can be prepared by reacting a compound of formula III

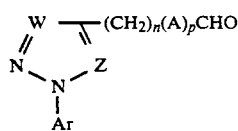
(III)

with a compound of formula $H_2N—CR^2=CR^3—NH_2$

The compound of formula III, where n and p are 0, W is CH and Z is N, can be prepared for example by ring closing a compound of formula IV

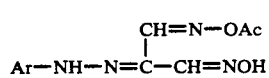
(IV)

in which Ac is an acyl group, eg using an alkali metal carbonate, followed by hydrolysis.

The compound of formula III, where n is 0 and p is 1 and A is —CH=CH—, can be prepared by reacting a compound of formula III, where n is 0 and p is 0, with a suitable phosphorane.

The compound of formula IV, can be prepared by acylation of a compound of formula V

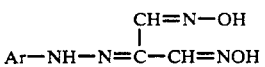
(V)

The compound of formula V can be formed by reaction of an arylhydrazine, $ArNHNH_2$, with a compound of formula VI

(VI)

The compound of formula III, where p is 0, can also be prepared by oxidation of an alcohol of formula VII

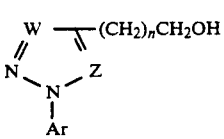
(VII)

by methods known in the art e.g. using pyridinium dichromate or manganese dioxide.

The compound of formula III, where p is 0, can also be prepared by reducing an ester of formula VIII

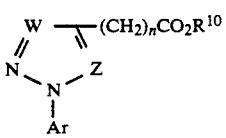
(VIII)

where $R^{10}$ is alkyl, eg using diisobutylaluminium hydride in an inert solvent at very low temperature.

The compound of formula VII can be prepared by reduction of the ester of formula VIII, by methods known in the art e.g. using lithium aluminium hydride, diisobutylaluminium hydride or zirconium borohydride (prepared in situ from zirconium tetrachloride and sodium borohydride) in an inert solvent, such as tetrahydrofuran.

The compound of formula VII can also be prepared by reduction of a carboxylic acid of formula VIII, where $R^{10}$ is H, by known methods.

The compound of formula VII in which W is N and Z is $CR^5$ can be prepared by the cycloaddition of an acetylene of formula IX

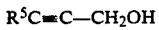
(IX)

with an aryl azide, $ArN_3$, or by reduction of an ester VIII, where W is N, Z is $CR^5$ and $R^{10}$ is alkyl, formed by reaction of an aryl azide with an ester of formula X

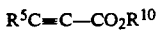
(X)

A compound of formula VIII where Z is N, W is $CR^1$ and $R^{10}$ is H, may be prepared from a compound of formula VIII, where Z is N, W is $CR^1$ and $R^{10}$ is alkyl or aryl, by hydrolysis or from a compound of formula XI

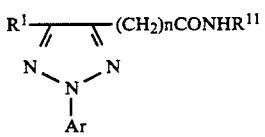
(XI)

in which $R^{11}$ is alkyl or aryl by initial reaction with e.g. di-tert-butyl carbonate, followed by hydrolysis.

A compound of formula VIII or IX, where n is 0, Z is N, W is $CR^1$ and $R^{10}$ and $R^{11}$ are alkyl or aryl or a compound of formula XI may be prepared by cyclisation of a compound of formula XII $$Ar-NH-N=\underset{\underset{N-OAc}{\|}}{\overset{\overset{R^1}{|}}{C}}-C-Q \qquad (XII)$$

in which Q is $CONHR^{11}$ or $CO_2R^{10}$ using a base such as an alkali metal carbonate.

Alternatively, a compound of formula VIII, where n is 0, Z is N, W is $CR^1$ and $R^{10}$ is alkyl or aryl, may be prepared by cyclisation of a compound of formula XIIa $$Ar-NH-N=\underset{\underset{N-OAc}{\|}}{\overset{\overset{COOR^{10}}{|}}{C}}-C-R^1 \qquad (XIIa)$$

using a base such as an alkali metal carbonate.

A compound of formula XII may be prepared by reaction of an arylhydrazine with a compound of formula XIII $$R^1CO-\underset{\underset{N-OH}{\|}}{C}-Q \qquad (XIII)$$

and subsequent acylation.

A compound of formula XIIa may be prepared by reacting a compound of formula XIIb $$Ar-NH-N=\underset{\underset{O}{\|}}{\overset{\overset{COOR^{10}}{|}}{C}}-C-R^1 \qquad (XIIb)$$

with hydroxylamine and acylating the oxime, so obtained.

The compound of formula XIIb may be prepared by diazotisation of an aniline, $Ar-NH_2$, and reacting the resulting diazonium salt with a β-keto ester of formula XIIc $$R^1CO-CH_2-COOR^{10} \qquad (XIIc)$$

A compound of formula VIII, where n is 0, W is $CR^1$, Z is $CR^5$ and $R^5$ is amino, may be prepared by reaction of a phenylhydrazine $$ArNHNH_2$$

with a compound of formula $$\underset{alkoxy}{\overset{R^1}{\diagdown}}C=C\underset{CN}{\overset{COOR^{10}}{\diagup}}$$

or when $R^1$ is alkylthio, with a compound of formula $$\underset{R^1}{\overset{R^1}{\diagdown}}C=C\underset{CN}{\overset{COOR^{10}}{\diagup}}$$

A compound of formula I, where $R^6$ and $R^7$ form a bond and $R^2$, $R^3$ and $R^4$ are hydrogen may be modified by known methods such as e.g. electrophilic substitution reactions to give compounds of formula I where $R^2$ and/or $R^3$ are e.g. halogen, nitro etc. These groups may be modified by methods known to those skilled in the art to give other $R^2$ and $R^3$ groups. In some cases it may be necessary to have a suitable protecting group at $R^4$, which can subsequently be removed, in known manner.

A compound of formula I, where p is 0, $R^6$ and $R^7$ form a bond and $R^2$, $R^3$ and $R^4$ are hydrogen may be obtained by reaction of a compound of formula XV $$\underset{\underset{Ar}{|}}{\overset{W}{\underset{N}{\diagup\!\!\diagdown}}}\!\!\!\!\!\!\!\!\!\!\!\!\!\underset{N}{\overset{(CH_2)_nC}{\diagdown}}\underset{OEt}{\overset{NH}{\diagup}}\cdot HCl \qquad (XV)$$

with a compound of formula XVI $$H_2N-CH_2-CH(OMe)_2 \qquad (XVI)$$

The compound of formula XV may be prepared from a compound of formula XVII $$\underset{\underset{Ar}{|}}{\overset{W}{\underset{N}{\diagup\!\!\diagdown}}}\!\!\!\!\!\!\!\!\!\!\!\!\!(CH_2)_nCN \qquad (XVII)$$

by reaction with e.g. gaseous hydrogen chloride in ethanol.

The preparation of compounds of formula XVII, where W is $CR^1$ and Z is N, is described in EP 350 237.

A compound of formula I in which A is O, S or NH and $R^6$ and $R^7$ form a bond may be prepared by reaction of a compound of formula XVIII $$\underset{\underset{Ar}{|}}{\overset{W}{\underset{N}{\diagup\!\!\diagdown}}}\!\!\!\!\!\!\!\!\!\!\!\!\!(CH_2)_nAH \qquad (XVIII)$$

with a compound of formula XIX $$R^{12}\!\!-\!\!\underset{\underset{R^4}{|}}{\overset{N}{\diagup\!\!\diagdown}}\!\!\!\!\!\!\!\!\!\!\!\!\!\underset{N}{\overset{R^2}{\diagdown}}\!\!\!R^3 \qquad (XIX)$$

in which $R^{12}$ is a leaving group, such as a halogen.

A compound of formula I, where p is 0, $R^6$ and $R^7$ for a bond and $R^3$ and $R^4$ are hydrogen may be obtained by reaction of a compound of formula III, with a compound of formula R²—CO—CHBr₂ and ammonia.

Where, in a compound of formula XIX, the group R⁴ is a protecting group, e.g. containing silicon, the resulting compound of formula I may be optionally further modified in known manner, e.g. by hydrolysis or reaction with a source of fluoride ion to give compounds of formula I in which R⁴ is H.

A compound of formula XIX may be formed from a compound of formula XX

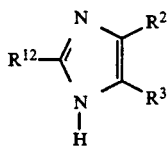

(XX)

by a variety of known methods, eg as described in "Protective Groups in Organic Synthesis" by T W Greene, published by John Wiley and Sons.

The preparation of compounds of formula XVIII in which W is CR¹ and Z is N is disclosed in E 350 237.

The compound of formula III, where n and p are 0, W is CR¹, Z is CR⁵, in which R⁵ is chlorine or bromine can be prepared for example by reacting a compound of formula XXI

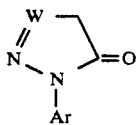

(XXI)

with dimethylformamide in the presence of phosphorus oxychloride or phosphorus oxybromide to give respectively the compounds where R⁵ is chlorine or bromine.

A compound of formula XXI, where W is CR¹, may be prepared in known manner by reaction of an arylhydrazine with a compound of formula XIIc.

The compound of formula III, where n and p are 0, W is CR¹, Z is CR⁵, in which R¹ and R⁵ are the same alkyl, can be prepared for example by reacting a compound of formula XXIa

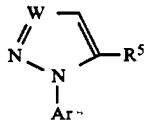

(XXIa)

with dimethylformamide in the presence of phosphorus oxychloride.

The compound of formula XXIa can be formed by reaction of an arylhydrazine, ArNHNH₂, with a compound of formula XXIb R⁵COCH₂COR⁵    (XXIb)

The compound of formula III, where p is 0, W is CR¹, Z is CNRᵃRᵇ, in which Rᵃ and Rᵇ are alkyl or acyl, can be prepared for example by reacting a compound of formula XXIc

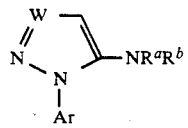

(XXIc)

with a phosphorus oxychloride and dimethylformamide.

The compound of formula XXIc may be prepared by reacting the compound of formula XXId

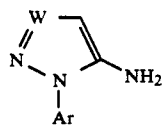

(XXId)

with a suitable alkyl or acyl halide, in the presence of a base.

A compound of formula I in which R⁴ is H and R⁶ and R⁷ form a bond or in which R⁷ is H and R⁴ and R⁶ form a bond may be further modified in known manner, e.g. by alkylation to give other R⁴ groups.

A compound of formula I, where n is 2 and p is 0, may be prepared by reducing, in known manner a compound of formula I where n is 0, p is 1 and A is —CH=CH—.

A compound of formula I, where Z is N, W is CR¹ and R¹ is halogen, and n and p are 0, may be obtained by reaction of the 2-oxide of the compound of formula I, where W is CH with an acyl halide. This compound can itself be obtained from the corresponding 4-carboxaldehyde, in a similar manner to that described for converting the compound of formula III to formula I. This compound can be obtained by oxidative ring closure, eg using copper sulphate, followed by hydrolysis of the resulting 4-carboxaldehyde oxime.

When compounds are obtained where W is CR¹ and Z is CNH₂, the amino group may be modified in known manner to give other desired values for R⁵.

Other methods will be apparent from the Examples given hereinafter.

It will be evident to those skilled in the art that in compounds of formula I where R² and R³ are different, tautomeric forms exist where either R⁴ and R⁶ form a bond and R⁷ is H or R⁶ and R⁷ form a bond and R⁴ is H. These tautomers and any mixture thereof form part of the invention. Similarly in compounds of formula I where R² and R³ are different and R⁴ and R⁷ are different, then isomers are possible—for example compounds in which R² and R³ are different and R⁶ and R⁷ form a bond and R⁴ is a group R¹⁴ which is not hydrogen are isomeric with the corresponding compounds in which R⁴ and R⁶ form a bond and R⁷ is R¹⁴. These isomers and any mixture thereof comprise part of the invention.

The compounds of formula I in which either R⁶ and R⁷ form a bond and R⁴ is hydrogen or R⁴ and R⁶ form a bond and R⁷ is hydrogen may form pesticidally and pharmaceutically acceptable salts with organic or inorganic bases, especially where R² and/or R³ are electron withdrawing groups. These salts also form part of the invention.

Pesticidally acceptable salts means salts, the cations of which are known and accepted in the art as being suitable for the formation of salts of pesticidally active acids for use in agriculture or horticulture.

Similarly, pharmaceutically acceptable salts means salts, the cations of which are known and accepted in the art as being suitable for the formation of salts of biologically active acids for use in veterinary or human medicine.

Generally the salt is an alkali metal, alkaline earth metal, quaternary ammonium or an amine salt. Amine salts include salts derived from primary, secondary and tertiary amines, including amino sugars, such as N-methylglucamine. Salts may be prepared by reacting the compound of the invention, in known manner, with a suitable base.

The invention is illustrated in the following examples. Structures of isolated novel compounds were confirmed by elemental and/or other appropriate analyses. Temperatures are in °C. The preparation of many starting materials which are 2-substituted 2H-1,2,3-triazoles is disclosed in our EP 350 237.

EXAMPLE 1

A mixture of 2,6-dichloro-4-trifluoromethylphenylhydrazine (34 g), 2-oxopropanedial 1,3-dioxime (17 g) and ethanol (300 ml) was heated under reflux for 3½ hours. The solvent was evaporated under reduced pressure and the residue triturated with light petroleum (bp 40°-60°) and filtered to give 2-oxopropanedial 2-(2,6-dichloro-4-trifluoromethylphenylhydrazone) 1,3-dioxime.

This product (36 g) was stirred in acetic anhydride (350 ml) and acetic acid (220 ml) at room temperature for 45 mins. The mixture was poured into water and filtered and the residue dried in vacuo at 40° to give 2-oxopropanedial 1-acetyloxime 2-(2,6-dichloro-4-trifluoromethylphenylhydrazone) 3-oxime. A mixture of this product (38.5 g) and caesium carbonate (32.6 g) in tetrahydrofuran (1000 ml) was stirred at room temperature for 1½ hours. The solvent was evaporated under reduced pressure and the residue taken up in ether. The extract was washed with water, dried and evaporated. The residue was triturated with light petroleum (bp 40°-60°) and filtered to give 2-(2,6-dichloro-4-trifluoromethylphenyl)-2H-1,2,3-triazole-4-carboxaldehyde oxime.

This product (26.3 g) was heated under reflux with 1,3,5-trioxane and 2 molar hydrochloric acid (1000 ml) for 4 hours. The mixture was extracted with ether and the extract washed with water, dried and evaporated. The residue was purified by column chromatography to give 2-(2,6-dichloro-4-trifluoromethylphenyl)-2H-1,2,3-triazole-4-carboxaldehyde, m.p. 94°-95°.

This product (3 g) was added with stirring to a solution of diaminomaleonitrile (1.1 g) in methanol (15 ml) and the mixture stirred at room temperature for 1½ hours and then heated under reflux for 1 hour. It was then cooled and the solid filtered off and recrystallised from acetonitrile to give 2-(2,6-dichloro-4-trifluoromethylphenyl)-4-[(2-amino-1,2-dicyanoethenylimino)methyl]-2H-1,2,3-triazole, mp 234°-235°.

A solution of this product (5 g) and 2,3-dichloro-5,6-dicyano-1,4-benzoquinone (4.23 g) in acetonitrile (100 ml) was heated under reflux for 12 hours. The solvent was removed under reduced pressure and the residue was purified by column chromatography followed by trituration with hexane to give 2-(2,6-dichloro-4-trifluoromethylphenyl)-4-(4,5-dicyano-1H-imidazol-2-yl)-2H-1,2,3-triazole, m.p. 192°-194°. (Compound 1a).

In a similar manner a) 2,6-dichloro-4-trifluoromethoxyphenylhydrazine gave
  (i)  2-(2,6-dichloro-4-trifluoromethoxyphenyl)-2H-1,2,3-triazole-4-carboxaldehyde, m.p. 73°-75°, which was converted to
  (ii) 2-(2,6-dichloro-4-trifluoromethoxyphenyl)-4-[(2-amino-1,2-dicyanoethenylimino)methyl]-2H-1,2,3-triazole, m.p. 199°-201°, which in turn gave
  (iii) 2-(2,6-dichloro-4-trifluoromethoxyphenyl)-4-(4,5-dicyano-1H-imidazol-2-yl)-2H-1,2,3-triazole, m.p. 93°-96°. (Compound 1b);
b) 2,4,6-trichlorophenylhydrazine gave
  (i)  2-(2,4,6-trichlorophenyl)-2H-1,2,3-triazole-4-carboxaldehyde, m.p. 68°-70°, which was converted to
  (ii) crude 4-[(2-amino-1,2-dicyanoethenylimino)methyl]-2-(2,4,6-trichlorophenyl)-2H-1,2,3-triazole, which in turn gave
  (iii) 4-(4,5-dicyano-1H-imidazol-2-yl)-2-(2,4,6-trichlorophenyl)-2H-1,2,3-triazole, m.p. 215°. (Compound 1c);
c) 3-chloro-5-trifluoromethyl-2-pyridylhydrazine gave
  (i) 2-(3-chloro-5-trifluoromethyl-2-pyridyl)-2H-1,2,3-triazole-4-carboxaldehyde, m.p. 78°-82°, which was converted to
  (ii) 2-(3-chloro-5-trifluoromethyl-2-pyridyl)-4-[(2-amino-1,2-dicyanoethenylimino)methyl]-2H-1,2,3-triazole, m.p. 220°-222°, which in turn gave
  (iii) 2-(3-chloro-5-trifluoromethyl-2-pyridyl)-4-(4,5-dicyano-1H-imidazol-2-yl)-2H-1,2,3-triazole, m.p. 189°-193°. (Compound 1d);
d) 4-bromo-2,6-dichlorophenylhydrazine gave
  (i) 2-(4-bromo-2,6-dichlorophenyl)-2H-1,2,3-triazole-4-carboxaldehyde, m/z 321(M+; 85%), which was converted to
  (ii) 2-(4-bromo-2,6-dichlorophenyl)-4-[(2-amino-1,2-dicyanoethenylimino)methyl]-2H-1,2,3-triazole, obtained as a crude oil, which in turn gave
  (iii) 2-(4-bromo-2,6-dichlorophenyl)-4-(4,5-dicyano-1H-imidazol-2-yl)-2H-1,2,3-triazole, mp 173°-175°. (Compound 1e);
e) 2-nitro-4-trifluoromethylphenylhydrazine gave
  (i) 2-(2-nitro-4-trifluoromethylphenyl)-2H-1,2,3-triazole-4-carboxaldehyde, as a crude oil, which was converted to
  (ii) 2-(2-nitro-4-trifluoromethylphenyl)-4-[(2-amino-1,2-dicyanoethenyl)iminomethyl]-2H-1,2,3-triazole, m/z 376 (M+; 30%), which in turn gave
  (iii) 2-(2-nitro-4-trifluoromethylphenyl)-4-(4,5-dicyano-1H-imidazol-2-yl)-2H-1,2,3-triazole, m.p. 136°-138°. (Compound 1f);
f) 2,4,6-trifluorophenylhydrazine gave
  (i) 2-(2,4,6-trifluorophenyl)-2H-1,2,3-triazole-4-carboxaldehyde, m.p. 79°-82°, which was converted to
  (ii) 2-(2,4,6-trifluorophenyl)-4-[(2-amino-1,2-dicyanoethenylimino)methyl]-2H-1,2,3-triazole, m.p. 213°-215°, which in turn gave
  (iii) 2-(2,4,6-trifluorophenyl)-4-(4,5-dicyano-1H-imidazol-2-yl)-2H-1,2,3-triazole, m.p. 168°-172°. (Compound 1g);

EXAMPLE 1a

This example illustrates an alternative process for preparing compound 1a.

A mixture of 2-(2,6-dichloro-4-trifluoromethylphenyl)-4-[(2-amino-1,2-dicyanoethenylimino)methyl]-

2H-1,2,3-triazole (4.5 g), nicotinamide (1.6 g) and N-chlorosuccinimide (3 g) in dimethylformamide (30 ml) was stirred at 55°-65° for 1 hour. The mixture was poured onto water and the resulting solid was dissolved in ether, washed with water, treated with charcoal and dried. Evaporation of solvent gave a glassy solid. This was treated with sodium hydroxide solution (66 g in 150 ml) and the mixture was filtered. The filtrate was acidified and the white solid was filtered off and dried to give compound 1a.

EXAMPLE 2

A mixture of compound 1a (2.3 g), sodium hydroxide (0.4 g), water (30 ml), tetrahydrofuran (10 ml), and dimethyl sulphate (0.73 g) was stirred at room temperature for 9 hours. The mixture was poured into water, extracted with ether and the extract worked up to give 2-(2,6-dichloro-4-trifluoromethylphenyl)-4-(4,5-dicyano-1-methyl-1H-imidazol-2-yl)-2H-1,2,3-triazole, m.p. 154°-156°. (Compound 2a). 607155

In a similar manner compound 1a was reacted with chloromethyl pivalate, in the presence of potassium carbonate to give 2-(2,6-dichloro-4-trifluoromethyl-phenyl)-4-(4,5-dicyano-1-pivaloyloxymethyl-1H-imidazol-2-yl)-2H-1,2,3-triazole, m.p. 103°-104°. (Compound 2b).

EXAMPLE 3

A mixture of compound 1a (0.25 g) and N-methyl-D-glucamine (0.123 g) was suspended in water (20 ml), placed in a sonic bath for 10 minutes and filtered. The filtrate was freeze dried to give the N-methyl-D-glucamine salt of 2-(2,6-dichloro-4-trifluoromethylphenyl)-4-(4,5-dicyano-1H-imidazol-2-yl)-2H-1,2,3-triazole, m.p. >250° (dec.) (Compound 3a).

In a similar manner using sodium hydroxide there was obtained the sodium salt of 2-(2,6-dichloro-4-trifluoromethylphenyl)-4-(4,5-dicyano-1H-imidazol-2-yl)-2H-1,2,3-triazole, m.p. >250° (dec.) (Compound 3b).

EXAMPLE 4

Pyridinium dichromate (7.5 g) was added, with stirring, to a solution of crude [2-(2,6-dichloro-4-tri-fluoromethylphenyl)-5-methyl-2H-1,2,3-triazol-4-yl]methanol (4.3 g) in dichloromethane (50 ml) at room temperature. The mixture was stirred overnight and then ether (100 ml) and silica (4 g) was added. After 10 minutes, the mixture was filtered through a pad of magnesium sulphate and the solvent was evaporated to give 2-(2,6-dichloro-4-trifluoromethylphenyl)-5-methyl-2H-1,2,3-triazole-4-carboxaldehyde, as a crude brown solid. This product was then treated in similar manner to Example 1 with diaminomaleonitrile to give 2-(2,6-dichloro-4-trifluoromethylphenyl)-4-[(2-amino-1,2-dicyanoethenylimino)methyl]-5-methyl-2H-1,2,3-triazole, m.p. 238°-239°.

This product was then cyclised in a similar manner to Example 1 to give 2-(2,6-dichloro-4-trifluoromethyl-phenyl)-4-(4,5-dicyano-1H-imidazol-2-yl)-5-methyl-2H-1,2,3-triazole, m.p. 228°-229°. (Compound 4a).

In a similar manner
a) [2-(2-nitro-4-trifluoromethylphenyl)-5-methyl-2H-1,2,3-triazol-4-yl]methanol was converted to:
  (i) 2-(2-nitro-4-trifluoromethylphenyl)-5-methyl-2H-1,2,3-triazole-4-carboxaldehyde, m/z 300 (M+,100%), which was converted to:
  (ii) 2-(2-nitro-4-trifluoromethylphenyl)-4-[(2-amino-1,2-dicyanoethenylimino)methyl]-5-methyl-2H-1,2,3-triazole, m.p. 219°-221°, which in turn gave
  (iii) 2-(2-nitro-4-trifluoromethylphenyl)-4-(4,5-dicyano-1H-imidazol-2-yl)-5-methyl-2H-1,2,3-triazole, m.p. 182°-184°. (Compound 4b);
b) [2-(2,6-dichloro-4-trifluoromethylthiophenyl)-5-methyl-2H-1,2,3-triazol-4-yl]methanol was converted to:
  i) 2-(2,6-dichloro-4-trifluoromethylthiophenyl)-5-methyl-2H-1,2,3,-triazole-4-carboxaldehyde, m/z 355 (M+,100%), which was converted to:
  iii) 2-(2,6-dichloro-4-trifluoromethylthiophenyl)-4-[(2-amino-1,2-dicyanoethenylimino)methyl]-5-methyl-2H-1,2,3-triazole, m.p. 232°-234°, which in turn was cyclised to:
  iv) 2-(2,6-dichloro-4-trifluoromethylthiophenyl)-4-(4,5-dicyano-1H-imidazol-2-yl)-5-methyl-2H-1,2,3-triazole, m.p. 196°-197°. (Compound 4c)
c) Crude [2-(2,6-dichloro-4-trifluoromethylphenyl)-5-methylthiomethyl-2H-1,2,3-triazole-4-yl]methanol, was oxidised and then condensed with diaminomaleonitrile to give:
  i) 2-(2,6-dichloro-4-trifluoromethylphenyl)-4-[(2-amino-1,2-dicyanoethenylimino)methyl]-5-(methylthiomethyl)-2H-1,2,3-triazole, m.p. 237°-239°, which in turn gave:
  ii) 2-(2,6-dichloro-4-trifluoromethylphenyl)-4-(4,5-dicyano-1H-imidazol-2-yl)-5-(methylthiomethyl)-2H-1,2,3-triazole, m/z. 457(M+). (Compound 4d)
d) crude [2-(2,6-dichloro-4-trifluoromethylphenyl)-5-ethyl-2H-1,2,3-triazole-4-yl]methanol gave:
  i) 2-(2,6-dichloro-4-trifluoromethylphenyl)-5-ethyl-2H-1,2,3-triazole-4-carboxaldehyde, $n_D^{25} = 1.522$ which was converted to:
  ii) 2-(2,6-dichloro-4-trifluoromethylphenyl)-4-[(2-amino-1,2-dicyanoethenylimino)methyl]-5-ethyl-2H-1,2,3-triazole, m.p. 244°-246°, which in turn was cyclised to give:
  iii) 2-(2,6-dichloro-4-trifluoromethylphenyl)-4-(4,5-dicyano-1H-imidazol-2-yl)-5-ethyl-2H-1,2,3-triazole, m.p. 176°-178.5°. (Compound 4e)
e) [2-(2,6-dichloro-4-trifluoromethylphenyl)-5-trifluoromethyl-2H-1,2,3-triazole-4-yl]methanol, was converted to:
  i) 2-(2,6-dichloro-4-trifluoromethylphenyl)-5-tri-fluoromethyl-2H-1,2,3-triazole-4-carboxaldehyde m.p. 49°-51°, which was converted to:
  ii) 2-(2,6-dichloro-4-trifluoromethylphenyl)-4-[(2-amino-1,2-dicyanoethenylimino)methyl]-5-trifluoromethyl-2H-1,2,3-triazole, m.p. 218°-220°, which in turn gave
  iii) 2-(2,6-dichloro-4-trifluoromethylphenyl)-4-(4,5-dicyano-1H-imidazol-2-yl)-5-trifluoromethyl-2H-1,2,3-triazole, m.p. 115°-125° (dec.). (Compound 4f)

EXAMPLE 5

A solution of sodium nitrite (3.2 g) in concentrated sulphuric acid (22 ml) was added dropwise with cooling to a solution of 2,6-dichloro-4-trifluoromethylaniline (9.3 g) in glacial acetic acid (48 ml). The mixture was stirred at room temperature for half an hour and then cooled to 0°-5°. A solution of sodium azide (2.6 g) in the minimum volume of water was added dropwise with cooling and the mixture stirred at 0°-5° for 1 hour and then at room temperature overnight. The mixture was poured into ice/water, extracted with dichloromethane and the extract worked up in conventional manner to give 1-azido-2,6-dichloro-4-trifluoromethylbenzene, as a red oil. A solution of this oil (25.6 g) and 2-propyn-1-ol (40 ml) in xylene (80 ml) were stirred under nitrogen and heated under reflux overnight. The mixture was cooled and the solvent was evaporated under reduced pressure. Trituration of the residue with light petroleum (bp 30°-40°) gave a crude material which was purified by filtration through silica to give [1-(2,6-dichloro-4-trifluoromethylphenyl)-1H-1,2,3-triazol-4-yl]methanol, m.p.123°-125°.

A mixture of this alcohol (1.7 g) and manganese dioxide (6.9 g) in chloroform (40 ml) was stirred at room temperature for 24 hours. This mixture was then filtered through Kieselguhr and the solvent evaporated to give crude material, which was purified by flash column chromatography (silica) to give 1-(2,6-dichloro-4-trifluoromethylphenyl)-1H-1,2,3-triazole-4-carboxaldehyde, m.p 143°-144.5°. The aldehyde (2.32 g) and diaminomaleonitrile (0.85 g) were heated under reflux in methanol (40 ml) for 6 hours and then left to stand for 60 hours at room temperature. The solvent was evaporated and the residue was purified by column chromatography and recrystallisation from ethyl acetate/light petroleum (bp. 60°-80°) to give 1-(2,6-dichloro-4-trifluoromethylphenyl)-4-[(2-amino-1,2-dicyanoethenylimino)methyl]-1H-1,2,3-triazole, m.p.184°-186° (dec.).

This compound (1 g), was cyclised in similar manner to Example 1a to give, after recrystallisation from ethyl acetate/light petroleum (bp 60°-80°), 1-(2,6-dichloro-4-trifluoromethylphenyl)-4-(4,5-dicyano-1H-imidazol-2-yl)-1H-1,2,3-triazole, m.p. 236°-238°. (compound 5).

EXAMPLE 6

Dry hydrogen chloride was bubbled through a mixture of 2-(2,6-dichloro-4-trifluoromethylphenyl)-2H-1,2,3-triazole-4-carbonitrile (11 g), dry diethyl ether (70 ml) and absolute ethanol (3 ml) for 3 hours. A further quantity of absolute ethanol (3 ml) was added and the passage of dry hydrogen chloride was continued for 3 hours. The resulting white precipitate was filtered off and washed with ether and then dried under vacuum to give ethyl 2-(2,6-dichloro-4-trifluoromethylphenyl)-2H-1,2,3-triazole-4-carboximidate hydrochloride, m.p. 230°-231°.

This compound (4.6 g) was suspended in a mixture of tetrahydrofuran (50 ml) and dichloromethane (15 ml) and then 2,2-dimethoxyethylamine (1.3 g) was added. This mixture was stirred at room temperature for 50 minutes and then heated under reflux for 1 hour. Concentrated hydrochloric acid (2 ml) and 2M hydrochloric acid (6 ml) were added and the mixture was heated under reflux for 3½ hours. The solvent was evaporated and the residue was washed with diethyl ether and then dichloromethane. The resulting solid was treated with aqueous sodium carbonate solution and extracted with ethyl acetate. Evaporation of solvent gave 2-(2,6-dichloro-4-trifluoromethylphenyl)-4-(1H-imidazol-2-yl)-2H-1,2,3-triazole, m.p. 282°-283°. (Compound 6a)

N-Bromosuccinimide (1.44 g) was added portionwise to a solution of the above triazole (1.4 g) in chloroform (60 ml) with stirring. The mixture was stirred for 3 hours at room temperature and then the solvent was evaporated. The residue was purified by flash column chromatography to give 2-(2,6-dichloro-4-trifluoromethylphenyl)-4-(4,5-dibromo-1H-imidazol-2-yl)-2H-1,2,3-triazole, m.p. 234°-235°. (Compound 6b).

EXAMPLE 7

Compound 6a (3.0 g), was added portionwise over 5 minutes to a stirred mixture of nitric acid (70%, 5 ml) and sulphuric acid (98%, 5 ml) and the temperature rose to 60°. Stirring was continued for 1 hour and then the mixture was stirred and heated at 60°-70° for 2 hours. The mixture was cooled and poured onto ice/water and then allowed to stand overnight. The resulting solid was filtered off, dried and recrystallised from diisopropyl ether to give 2-(2,6-dichloro-4-trifluoromethylphenyl)-4-(4-nitro-1H-imidazol-2-yl)-2H-1,2,3-triazole, m.p. 249°-250° (dec.). (compound 7).

EXAMPLE 8

A mixture of compound 7 (0.82 g), N-bromosuccinimide (0.4 g) and dimethylformamide (20 ml) was stirred at room temperature overnight. This mixture was then poured into water and the resulting solid was filtered off and dried. Recrystallisation from ethyl acetate/hexane gave 2-(2,6-dichloro-4-trifluoromethylphenyl)-4-(5-bromo-4-nitro-1H-imidazol-2-yl)-2H-1,2,3-triazole, m.p. 198°-199° (compound 8).

EXAMPLE 9

Crude 2-(2,6-dichloro-4-trifluoromethylphenyl)-5-methyl-2H-1,2,3-triazole-4-thiol, prepared as in EP 350 237, (10 g) in tetrahydrofuran (50 ml) was added to a stirred suspension of sodium hydride (80%, dispersion in oil, 1.0 g) in tetrahydrofuran (50 ml) at 0°. Then a solution of 2-bromo-4,5-dicyano-1-(2-trimethylsilylethoxymethyl)-1H-imidazole (10 g) in tetrahydrofuran (100 ml) was added, dropwise, with stirring at 0°-5°. The mixture was stirred at room temperature for 20 hours and then was poured into water and extracted with ethyl acetate. Conventional work-up and purification by column chromatography gave 2-(2,6-dichloro-4-trifluoromethylphenyl)-4-[4,5-dicyano-1-(2-trimethylsilylethoxymethyl)-1H-imidazol-2-ylthio]-5-methyl-2H-1,2,3-triazole, as a pale yellow oil, $n_D24°=1.526$ (compound 9a).

This compound (1.6 g) was dissolved in ethanol (50 ml) and hydrochloric acid (45 ml of concentrated acid and water (55 ml)) was added to give a white precipitate. The mixture was stirred and heated under reflux for 3 hours to give a clear solution. The solvent was evaporated, water was added and the mixture was extracted with ethyl acetate. Conventional work-up gave an oil, which was triturated with hexane. The resulting solid was recrystallised from ethyl acetate/hexane to give 2-(2,6-dichloro-4-trifluoromethylphenyl)-4-(4,5-dicyano-1H-imidazol-2-ylthio)-5-methyl-2H-1,2,3-triazole, m.p. 163°-165° (compound 9b).

EXAMPLE 10

2-(2,6-dichloro-4-trifluoromethylphenyl)-4-[(2-amino-1,2-dicyanoethenylimino)methyl]-2H-1,2,3-triazole (8 g) (prepared as in Example 1) was dissolved in methanol (50 ml) and tetrahydrofuran (75 ml) and then sodium borohydride (0.76 g) was added portionwise. This mixture was stirred for 20 minutes at room temperature and then poured into water to give a brown solid. This was purified by flash column chromatography to give 2-(2,6-dichloro-4-trifluoromethylphenyl)-4-[(2-amino-1,2-dicyanoethenylamino)methyl]-2H-1,2,3-triazole, m.p. 191°-192°. A mixture of this compound (1.8 g), nicotinamide (0.6 g), N-chlorosuccinimide (0.6 g) and dimethylformamide was heated at 65°-70° for 10 minutes. The mixture was poured into water and extracted with diethyl ether. Conventional work-up and purification by flash column chromatography gave 2-(2,6-dichloro-4-trifluoromethylphenyl)-4-(4,5-dicyano-4-imidazolin-2-yl)-2H-1,2,3-triazole, m.p. 219°-220° (dec). (Compound 10).

EXAMPLE 11

A solution of 2,6-dichloro-4-trifluoromethylphenylhydrazine (10 g) and ethyl 2-cyano-3-ethoxyacrylate (7.0 g) in absolute ethanol (200 ml) was heated under reflux with stirring for 24 hours. Evaporation of solvent and recrystallisation from diisopropyl ether gave ethyl 5-amino-1-(2,6-dichloro-4-trifluoromethylphenyl)-1H-pyrazole-4-carboxylate, m.p. 131°-134°.

This compound (11.01 g) was dissolved in bromoform (55 ml) at room temperature with stirring and tert-butyl nitrite (9.2 g) was added portionwise. The temperature of the mixture rose from 14° to 40° during the addition. The resulting mixture was stirred overnight at room temperature and then the solvent was evaporated under reduced pressure. The residue was dissolved in dichloromethane and washed successively with sodium bicarbonate, sodium thiosulphate and water. The solvent was dried and evaporated to give a viscous oil, which was purified by flash column chromatography to give ethyl 5-bromo-1-(2,6-dichloro-4-trifluoromethylphenyl)-1H-pyrazole-4-carboxylate m.p. 80°-82°.

In a similar manner to that described in EP 350 237, this ester was reduced with diisobutylaluminium hydride to give crude [5-bromo-1-(2,6-dichloro-4-trifluoromethylphenyl)-1H-pyrazol-4-yl]methanol, which was oxidised in a similar manner to that described in Example 4, to give 5-bromo-1-(2,6-dichloro-4-trifluoromethylphenyl)-1H-pyrazole-4-carboxaldehyde, which was converted, as described in Example 1, to 5-bromo-1-(2,6-dichloro-4-trifluoromethylphenyl)-4-[(2-amino-1,2-dicyanoethenylimino)methyl]-1H-pyrazole, which was cyclised to give 5-bromo-1-(2,6-dichloro-4-trifluoromethylphenyl)-4-(4,5-dicyano-1H-imidazol-2-yl)-1H-pyrazole, m.p. 167°-170°. (compound 11a)

In a similar manner:

a) methyl 5-amino-1-(2,6-dichloro-4-trifluoromethylphenyl)-3-methylthio-1H-pyrazole-4-carboxylate, m.p. 124°-126° [formed by reaction of 2,6-dichloro-4-trifluoromethylphenylhydrazine with methyl 3,3-di(methylthio)-2-cyanoacrylate in refluxing ethanol] gave:

i) methyl-5-bromo-1-(2,6-dichloro-4-trifluoromethylphenyl)-3-methylthio-1H-pyrazole-4-carboxylate, m.p. 117°-120°, which was converted to:

ii) [5-bromo-1-(2,6-dichloro-4-trifluoromethylphenyl)-3-methylthio-1H-pyrazol-4-yl]methanol (oil) m/z (M+,436), which was converted to:

iii) 5-bromo-1-(2,6-dichloro-4-trifluoromethylphenyl)-3-methylthio-1H-pyrazole-4-carboxaldehyde, m.p. 109°-112°, which was converted to:

iv) 5-bromo-1-(2,6-dichloro-4-trifluoromethylphenyl)-4-[(2-amino-1,2-dicyanoethenylimino) methyl]-3-methylthio-1H-pyrazole, m.p. 232°-235° which in turn was cyclised to give:

v) 5-bromo-1-(2,6-dichloro-4-trifluoromethylphenyl)-4-(4,5-dicyano-1H-imidazol-2-yl)-3-methylthio-1H-pyrazole, m.p. 196°-198°. (Compound 11b)

EXAMPLE 12

1,1-Dibromo-3,3,3-trifluoroacetone (4 g) was added to a solution of sodium acetate trihydrate (4 g) in water (20 ml) and the resulting solution heated on a steam bath for 30 mins. The mixture was cooled to room temperature and added slowly to a solution of 2-(2,6-dichloro-4-trifluoromethylphenyl)-2H-1,2,3-triazole-4-carboxaldehyde (3.7 g) (from Example 1) and aqueous ammonia (20 ml) in methanol (40 ml). The suspension was allowed to stand overnight. The supernatant liquid was decanted from the resulting gum, reduced in volume and poured into water to give a white precipitate which was collected by filtration, and dried to give 2-(2,6-dichloro-4-trifluoromethylphenyl)-4-(4-trifluoromethyl-1H-imidazol-2-yl)-2H-1,2,3-triazole, m.p. 262°-264°. (Compound 12).

EXAMPLE 13

Compound 12 (1 g) was heated at 70° C. in 5% aqueous ammonia in ethanol (20 ml) for 6 hours. The mixture was cooled and acidified with glacial acetic acid. The resulting white precipitate was filtered and dried to give 2,6-dichloro-4-trifluoromethylphenyl)-4-(4-cyano-1H-imidazol-2-yl)-2H-1,2,3-triazole, m.p. 250°-251°. (Compound 13)

EXAMPLE 14

In a similar manner to Example 8, a) Compound 12 was brominated to give 2,6-dichloro-4-trifluoromethylphenyl)-4-(5-bromo-4-trifluoromethyl-1H-imidazol-2-yl)-2H-1,2,3-triazole, m.p. 227°-229°. (Compound 14a), and b) Compound 13 was brominated to give 2,6-dichloro-4-trifluoromethylphenyl)-4-(5-bromo-4-cyano-1H-imidazol-2-yl)-2H-1,2,3-triazole, m.p. 215°-216°.(Compound 14b)

EXAMPLE 15

A solution of 2,6-dichloro-4-trifluoromethylphenylhydrazine (5.0 g), 2,4-pentanedione (2.1 ml) and conc. sulphuric acid (0.8 ml) in ethanol (40 ml) was heated under reflux for 20 hours. The ethanol was evaporated under reduced pressure and the residue dissolved in dichloromethane. The extract was washed with sodium bicarbonate solution and brine, dried over magnesium sulphate and evaporated to give 3,5-dimethyl-1-(2,6-dichloro-4-trifluoromethylphenyl)-1H-pyrazole.

This product (4.73 g) was dissolved in dimethylformamide (1.2 ml) and heated to 95°. Phosphorous oxychloride (1.45 ml) was added over 45 minutes and heating was continued for 3 hours. The mixture was poured into ice water, made basic with sodium bicarbonate and extracted with ether. The ether extract was washed with water, dried over magnesium sulphate and evaporated to give 3,5-dimethyl-1-(2,6-dichloro-4-trifluoromethylphenyl)pyrazole-4-carboxaldehyde, m.p. 82°-83°.

This product (2.83 g) was treated in a similar manner to Example 1 with diaminomaleonitrile to give 4-[(2-amino-1,2-dicyanoethenylimino)methyl]-1-(2,6-dichloro-4-trifluoromethylphenyl)-3,5-dimethylpyrazole, m.p. 237°-40°.

This product was then cyclised in a similar manner to Example 1 to give 1-(2,6-dichloro-4-trifluoromethylphenyl)-4-(4,5-dicyano-1H-imidazol-2-yl)-3,5-dimethylpyrazole, m.p. 80°-83°. (Compound 15)

EXAMPLE 16

Compound 4c (0.6 g) was oxidised with m-chloroperbenzoic acid (1.1 g) in dichloromethane (20 ml) to give 2-(2,6-dichloro-4-trifluoromethylsulphonylphenyl)-4-(4,5-dicyano-1H-imidazol-2-yl)-5-methyl-2H-1,2,3-triazole, m.p. 244°–245°. (Compound 16)

EXAMPLE 17

A mixture of compound 8 (2.0 g), sodium hydride (0.22 g) and dimethylformamide (30 ml) was stirred for 10 minutes. Chloromethyl 2-trimethylsilylethyl ether (0.7 g) was then added and the mixture stirred at room temperature overnight. It was poured into water and extracted with ethyl acetate. The extract was washed, dried and the solvent removed at reduced pressure. The resulting solid was purified by silica gel column chromatography to give 2-(2,6-dichloro-4-trifluoromethylphenyl)-4-[4-nitro-5-bromo-1-(2-trimethylsilylethoxymethyl)-1H-imidazol-2-yl]-2H-1,2,3-triazole, m.p. 126°–128°.

This compound (0.5 g) was stirred with sodium methanethiolate (0.06 g) in dimethylformamide (5 ml) for 18 hours, and the reaction mixture then poured into water and extracted with ethyl acetate. The extract was worked up to give 2-(2,6-dichloro-4-trifluoromethylphenyl)-4-[4-nitro-5-methylthio-1-(2-trimethylsilylethoxymethyl)-1H-imidazol-2-yl]-2H-1,2,3-triazole, which was further treated with tetrabutylammonium fluoride (1 ml, 1 molar solution) in tetrahydrofuran (5 ml) at reflux for 2 hours. The reaction mixture was poured into water and extracted with ethyl acetate. The extract was dried and the solvent removed at reduced pressure to yield a gum which was purified by silica gel column chromatography to give 2-(2,6-dichloro-4-trifluoromethylphenyl)-4-(4-nitro-5-methylthio-1H-imidazol-2-yl)-2H-1,2,3-triazole, m.p. 153°–155°. (Compound 17)

EXAMPLE 18

2-(2,6-Dichloro-4-trifluoromethylphenyl)-2H-1,2,3-triazole-4-carboxaldehyde (5.5 g) and aqueous ammonia (40 ml, 33%) were stirred in methanol (80 ml) while a 40% aqueous solution of pyruvic aldehyde (18 ml) was added slowly. The mixture was stirred at room temperature overnight, poured into water and extracted with ethyl acetate. The extract was worked up to give 2-(2,6-dichloro-4-trifluoromethylphenyl)-4-(4-methyl-1H-imidazol-2-yl)-2H-1,2,3-triazole, m.p. 217°–218°. (Compound 18)

EXAMPLE 19

Compound 18 was nitrated in a manner similar to Example 7 to give 2-(2,6-dichloro-4-trifluoromethylphenyl)-4-(4-methyl-5-nitro-1H-imidazol-2-yl)-2H-1,2,3-triazole, mp 231°–232°. (Compound 19)

EXAMPLE 20

Compound 18 (1.0 g) was heated in chlorosulphonic acid (4 ml) at 95° for 3 hours. The mixture was cooled and thionyl chloride (0.5 ml) added before heating at 100° for a further 2 hours. The mixture was cooled and poured onto ice. The white solid was collected by filtration and purified by silica gel column chromatography to give 2-(2,6-dichloro-4-trifluoromethylphenyl)-4-(4-methyl-5-chlorosulphonyl-1H-imidazol-2-yl)-2H-1,2,3-triazole, mp 254°–255°. (Compound 20)

EXAMPLE 21

2-Oxopropanedial-Z-(2,6-dichloro-4-trifluoromethylphenylhydrazone)-1,2-dioxime (28.8 g) was dissolved in pyridine (400 ml). A solution of copper (II) sulphate (42 g) in water (200 ml) was added slowly and the resulting mixture heated at 60° for 3.5 hours. The mixture was poured onto ice, made acidic (6M HCl) and extracted with diethyl ether. The extract was washed with water, dried and the solvent evaporated under reduced pressure to give 2-(2,6-dichloro-4-trifluoromethylphenyl)-2H-1,2,3-triazole-4-carboxaldehyde oxime 1-oxide, mp 171°–172°.

This compound (16 g) was heated under reflux overnight with trioxane (4.2 g) in 2N HCl (700 ml). The mixture was cooled and extracted with ethyl acetate. The extract was worked up to give an orange oil, which was purified by silica gel column chromatography to give 2-(2,6-dichloro-4-trifluoromethylphenyl)-2H-1,2,3-triazole-4-carboxaldehyde 1-oxide, m.p. 123°–125°.

This compound (13 g) was stirred with diaminomaleonitrile (4.4 g) in methanol for 5 hours. The brown solid formed during the reaction was filtered off and further purified by silica gel column chromatography to give 2-(2,6-dichloro-4-trifluoromethylphenyl)-4-[(2-amino-1,2-dicyanoethenylimino)methyl]-2H-1,2,3-triazole 1-oxide, m.p. 215°–216°.

This compound (4 g) was cyclised in a similar manner to Example 1a to give 2-(2,6-dichloro-4-trifluoromethylphenyl)-4-(4,5-dicyano-1H-imidazol-2-yl)-2H-1,2,3-triazole 1-oxide, m.p. 295°–296°. This compound (0.95 g) was stirred in acetyl chloride (10 ml) at room temperature for 3 hours. The solvent was removed under reduced pressure and the residue poured into water. The resulting white solid was collected by filtration and dried and recrystallised from hexane/ethyl acetate to give 2-(2,6-dichloro-4-trifluoromethylphenyl)-5-chloro-4-(4,5-dicyano-1H-imidazol-2-yl)-2H-1,2,3-triazole, m.p. 206°–208°. (Compound 21)

EXAMPLE 22

2,6-Dichloro-4-trifluoromethylphenylhydrazine (8 g) and ethyl 4-methyl-3-oxopentanoate (5.3 ml) were heated under reflux in glacial acetic acid for 3½ hours. The solvent was removed under reduced pressure and the resulting oil triturated with hexane to give 1-(2,6-dichloro-4-trifluoromethylphenyl)-3-isopropyl-1H-pyrazolin-5(4H)-one, mp 133°–135°. This compound (6.8 g) was added to a preformed mixture of phosphorus oxychloride (70 ml) and dimethylformamide (1.7 g). The resulting mixture was then heated under reflux for 30 minutes and the excess phosphorus oxychloride removed under reduced pressure. The residue was then poured carefully into water and extracted with diethyl ether. The extract was worked up to give an oil which was purified by silica gel column chromatography to give 1-(2,6-dichloro-4-trifluoromethylphenyl)-3-isopropyl-4-[(dimethylamino)methylidene]-1H-pyrazolin-5-one, m/z 393 (M+,100%).

This compound (1.0 g) was heated under reflux in phosphorus oxychloride (50 ml) for 2 hours and the mixture then stirred for a further 18 hours. Excess phosphorus oxychloride was removed under reduced pressure and the residue poured onto ice and extracted with diethyl ether. The extract was worked up to give an oil which was purified by silica gel column chromatography to give 5-chloro-1-(2,6-dichloro-4-trifluoromethylphenyl)-3-isopropyl-1H-pyrazole-4-carboxaldehyde, $n_D^{24} = 1.528$.

This compound (2.1 g) was treated with diaminomaleonitrile (0.6 g) in methanol (10 ml) in a similar manner to Example 1 to give 4-[(2-amino-1,2-dicyanoethenylimino)methyl]-5-chloro-3-isopropyl-1H-pyrazole, m.p. 145°–150°, which in turn was cyclised in a similar manner to Example 1a, to give 5-chloro-1-(2,6,dichloro-4-trifluoromethylphenyl)-4-(4,5-dicyano-1H-imidazol-2-yl)-3-isopropyl-1H-pyrazole, $n_D^{24}$ 1 537. (Compound 22a)

In a similar manner:

a) 1-(2,6-dichloro-4-trifluoromethylphenyl)-3-tert-butyl-1H-pyrazolin-5-one [formed from 2,6-dichloro-4-trifluoromethylphenylhydrazine and ethyl 4,4-dimethyl-3-oxopentanoate in acetic acid] gave:
  i) 1-(2,6-dichloro-4-trifluoromethylphenyl)-4-[(dimethylamino)methylidene]-3-tert-butyl-1H-pyrazolin-5-one, m/z 407 (M+), which was converted to:
  ii) 5-chloro-1-(2,6-dichloro-4-trifluoromethylphenyl)-3-tert-butyl-1H-pyrazole-4-carboxaldehyde, m/z 398 (M±1), which was converted to:
  iii) 5-chloro-4-[(2-amino-1,2-dicyanoethenylimino)methyl]-1-(2,6-dichloro-4-trifluoromethylphenyl)-3-tert-butyl-1H-pyrazole, m.p. 168°–171°, which in turn was converted to:
  iv) 5-chloro-1-(2,6-dichloro-4-trifluoromethylphenyl)-4-(4,5-dicyano-1H-imidazol-2-yl)-3-tert-butyl-1H-pyrazole, m.p. 118°–121°. (Compound 22b);

b) 1-(2,6-dichloro-4-trifluoromethylphenyl)-3-methyl-1H-pyrazolin-5-one, m.p. 165°–169° [formed from 2,6-dichloro-4-trifluoromethylphenylhydrazine and ethyl acetoacetate in acetic acid] gave:
  i) 5-chloro-1-(2,6-dichloro-4-trifluoromethylphenyl)-3-methyl-1H-pyrazole-4-carboxaldehyde, m.p. 75°–77°, which was converted to:
  ii) 4-[(2-amino-1,2-dicyanoethenylimino)methyl]-5-chloro-3-methyl-1H-pyrazole, m.p. 197°–203°, which in turn was converted to:
  iii) 5-chloro-1-(2,6-dichloro-4-trifluoromethylphenyl)-4-(4,5-dicyano-1H-imidazol-2-yl)-3-methyl-1H-pyrazole, m.p. 89°–94°. (Compound 22c)

c) 1-(2,6-dichloro-4-trifluoromethylphenyl)-3-ethyl-1H-pyrazolin-5-one, m.p. 138°–139° [formed from 2,6-dichloro-4-trifluoromethylphenylhydrazine and ethyl 3-oxopentanoate in acetic acid] gave:
  i) 5-chloro-1-(2,6-dichloro-4-trifluoromethylphenyl)-3-ethyl-1H-pyrazole-4-carboxaldehyde, m.p. 39°–41° which was converted to:
  ii) 4-[(2-amino-1,2-dicyanoethenylimino)methyl]-5-chloro-3-ethyl-1H-pyrazole, m.p. 186°–189°, which in turn was converted to:
  iii) 5-chloro-1-(2,6-dichloro-4-trifluoromethylphenyl)-4-(4,5-dicyano-1H-imidazol-2-yl)-3-ethyl-1H-pyrazole, m.p. 74°–80°. (Compound 22d)

EXAMPLE 23

2-(2,6-Dichloro-4-trifluoromethylphenyl)-2H-1,2,3-triazole-4-carboxaldehyde (2 g) and formylmethylene triphenylphosphorane (1.9 g) were heated under reflux in toluene for 4 hours. After removal of the solvent at reduced pressure the resulting residue was purified by column chromatography to give 3-[(2,6-dichloro-4-trifluoromethylphenyl)-2H-1,2,3-triazol-4-yl]-2-propanol, m.p. 68°–69°. This compound (1.8 g) was than stirred with diaminomaleonitrile (0.6 g) in methanol containing a trace of p-toluenesulphonic acid for 4 hours. Removal of the solvent at reduced pressure and column chromatography gave 2-(2,6-dichloro-4-trifluoromethylphenyl)-4-[3-(2-amino-1,2-dicyanoethenylimino)-2-propenyl]-2H-1,2,3-triazole, m.p. 207°–209°.

This compound (2.1 g) was cyclised in a similar manner to Example 1a, to give 2-(2,6-dichloro-4-trifluoromethylphenyl)-4-[2-(4,5-dicyano-1H-imidazol-2-yl)vinyl]-2H-1,2,3-triazole, m.p. 111°–112°. (Compound 23)

EXAMPLE 24

2-(2,6-Dichloro-4-trifluoromethylphenyl)-4-mercaptomethyl-2H-1,2,3-triazole, prepared as in EP 350 237, (0.33 g) and sodium hydroxide (0.04 g) were stirred in dioxane (2 ml) and water (1 ml) at ice bath temperature. 1-Allyl-2-bromo-4,5-dicyanoimidazole (0.24 g) in dioxane was added and the mixture stirred at room temperature for 2 hours. Aqueous work up and silica gel column chromatography gave 2-(2,6-dichloro-4-trifluoromethylphenyl)-4-[(4,5-dicyano-1-allyl-1H-imidazol-2-ylthio)methyl]-2H-1,2,3-triazole, m.p. 125°–127°. (Compound 24a)

In a similar manner, using 1-benzyl-2-bromo-4,5-dicyanoimidazole, there was obtained 2-(2,6-dichloro-4-trifluoromethylphenyl)-4-[(4,5-dicyano-1-benzyl-1H-imidazol-2-ylthio)methyl]-2H-1,2,3-triazole, m.p. 131.5°–132.5°. (Compound 24b)

In a similar manner, starting from 2-(2,6-dichloro-4-trifluoromethylphenyl-4-hydroxy-2H-1,2,3-triazole, prepared as in EP 350 237, and using potassium carbonate as the base, there was obtained 2-(2,6-dichloro-4-trifluoromethylphenyl)-4-(4,5-dicyano-1-allyl-1H-imidazol-2-yloxy)-2H-1,2,3-triazole, m.p. 121°–131°. (Compound 24c)

EXAMPLE 25

Sodium cyanoborohydride (0.05 g) was added to a solution of 2-(2,6-dichloro-4-trifluoromethylphenyl)-1,2,3-triazole-4-carboxaldehyde (0.3 g), potassium hydroxide (0.04 g) and 2-amino-4,5-dicyanoimidazole (0.3 g) in methanol (20 ml). After 20 hours at room temperature, the solvent was evaporated under reduced pressure and the residue purified by silica gel chromatography to give 2-(2,6-dichloro-4-trifluoromethylphenyl)-4-[(4,5-dicyano-1H-imidazol-2-ylamino)methyl]-2H-1,2,3-triazole, m.p. 213°–215°. (Compound 25)

EXAMPLE 26

In a similar manner to Example 17, compound 1e was reacted with chloromethyl 2-trimethylsilylethyl ether to give 2-(4-bromo-2,6-dichlorophenyl)-4-[4,5-dicyano-1-(2-trimethylsilylethoxymethyl)-1H-imidazol-2-yl]-2H-1,2,3-triazole, as an oil.

This compound (0.73 g), in deoxygenated tetrahydrofuran, was heated under reflux with potassium cyanide (0.13 g) and tetrakis(triphenylphosphine)palladium (0.019 g) for 18 hours. Work-up of the reaction mixture gave 2-(4-cyano-2,6-dichlorophenyl)-4-[4,5-dicyano-1-(2-trimethylsilylethoxymethyl)-1H-imidazol-2-yl]-2H-1,2,3-triazole, as an oil, which was treated immediately with tetrabutylammonium fluoride in tetrahydrofuran at room temperature. Work-up of the reaction mixture gave 2-(4-cyano-2,6-dichlorophenyl)-4-(4,5-dicyano-1H-imidazol-2-yl)-2H-1,2,3-triazole, m.p. 183°–185°. (Compound 26)

EXAMPLE 27

In a similar manner to Example 3, there was obtained from compound 4a, a) the N-methyl-D-glucamine salt of 2-(2,6-dichloro-4-trifluoromethylphenyl)-4-(4,5-dicyano-1H-imidazol-2-yl)-5-methyl-2H-1,2,3-triazole, m.p. >250° (dec.) (Compound 27a), and b) the sodium salt of 2-(2,6-dichloro-4-trifluoromethylphenyl)-4-(4,5-dicyano-1H-imidazol-2-yl)-5-methyl-2H-1,2,3-triazole, m.p. >250° (dec.) (Compound 27b).

EXAMPLE 28

In a similar manner to Example 4, [1-(2,6-dichloro-4-trifluoromethylphenyl)-1H-pyrazol-4-yl]methanol was converted to i) 1-(2,6-dichloro-4-trifluoromethylphenyl)-1H-pyrazole-4-carboxaldehyde, m.p. 113–114, which was converted to:

ii) 4-[(2-amino-1,2-dicyanoethenylimino)methyl]-1-(2,6-dichloro-4-trifluoromethylphenyl)-1H-pyrazole, m.p. 181°–183°, which in turn was converted to:

iii) 1-(2,6-dichloro-4-trifluoromethylphenyl)-4-(4,5-dicyano-1H-imidazol-2-yl)-1H-pyrazole, m.p. 245°–248°. (Compound 28);

EXAMPLE 29

4-Bromomethyl-2-(2,6-dichloro-4-trifluoromethylphenyl)-2H-1,2,3-triazole, prepared as in EP 350 237, was treated with potassium cyanide in dimethyl sulphoxide at room temperature for two hours. The mixture was added to water and extracted with diethyl ether. The extract was worked up to give crude 2-(2,6-dichloro-4-trifluoromethylphenyl)-2H-1,2,3-triazol-4-ylacetonitrile. In a similar manner to Example 6, this compound was converted to 2-(2,6-dichloro-4-trifluoromethylphenyl)-4-[(1H-imidazol-2-yl)methyl]-2H-1,2,3-triazole,. (Compound 29a).

This was then nitrated in a similar manner to Example 1 to give 2-(2,6-dichloro-4-trifluoromethylphenyl)-4-[(1H-imidazol-2-yl)methyl]-2H-1,2,3-triazole, (Compound 29b).

EXAMPLE 30

2-(2,6-Dichloro-4-trifluoromethylphenyl)-4-[2,2-di(methylthio)ethyl]-2H-1,2,3-triazole was treated with N-bromosuccinimide in aqueous acetonitrile., After 10 minutes the mixture was added to water and extracted with diethyl ether. The extract was worked up to give crude 2-(2,6-dichloro-4-trifluoromethylphenyl)-2H-1,2,3-triazole-4-acetaldehyde. This was then treated with diaminomaleonitrile in a similar manner to Example 1, to give 2-(2,6-dichloro-4-trifluoromethyl-phenyl)-4-[2-(2-amino-1,2-dicyanoethenylimino)ethyl]-2H-1,2,3-triazole, which was cyclised in a similar manner to Example 1a, to give 2-(2,6-dichloro-4-trifluoromethylphenyl)-4-[(4,5-dicyano-1H-imidazol-2-yl)methyl]-2H-1,2,3-triazole (Compound 30).

EXAMPLE 31

1-(2,6-Dichloro-4-trifluoromethylphenyl)-5-amino-3-methyl-1H-pyrazole, was methylated using methyl iodide, in the presence of sodium hydride to give 1-(2,6-dichloro-4-trifluoromethylphenyl)-5-methylamino-3-methyl-1H-pyrazole, mp 120°–121°. This compound (3 g) was treated with a mixture of phosphorus oxychloride (2 ml) in dimethylformamide (5 ml) at 70° for 4 hours to give on work up crude 1-(2,6-dichloro-4-trifluoromethylphenyl)-5-(N-formyl-N-methylamino)-3-methyl-1H-pyrrazole, which was reacted with borane-methyl sulphide complex in tetrahydrofuran at reflux for 2 hours to give on work up 1-(2,6-dichloro-4-trifluoromethylphenyl)-5-dimethylamino)-3-methyl-1H-pyrazole, as an oil. This product (2 g) was again treated with a mixture of phosphorus oxychloride (2 ml) in dimethylformamide (5 ml) to give on work up 1-(2,6-dichloro-4-trifluoromethylphenyl)-5-(dimethylamino)-3-methyl-1H-pyrazole-4-carboxaldehyde, mp 111°–112°, which by the method of Example 1 was converted to: 4-[(2-amino-1,2-dicyanoethenylimino)methyl]-1-(2,6-dichloro-4-trifluoromethylphenyl)-5-dimethylamino-3-methyl-1H-pyrazole, mp 187°–188°, which in turn was cyclised, as in Example 1 to: 1-(2,6-dichloro-4-trifluoromethylphenyl)-4-(4,5-dicyano-1H-imidazol-2-yl)-5-dimethylamino-3-methyl-1H-pyrazole, mp 248°–250° (dec). (Compound 31).

EXAMPLE 32

5-Amino-1-(2,6-dichloro-4-trifluoromethylphenyl)-3-methyl-1H-pyrazole-4-carboxaldehyde, was converted by the method of Example 1 to: 5-amino-4-[(2amino-1,2-dicyanoethenylimino)methyl]-1-(2,6-dichloro-4-trifluoromethylphenyl)-3-methyl-1H-pyrazole, mp 187°–191° (dec), which in turn was cyclised, as in Example 1a to: 5-amino-1-(2,6-dichloro-4-trifluoromethylphenyl)-4-(4,5-dicyano-1H-imidazol-2-yl)-3-methyl-1H-pyrazole, mp >160° (dec) (Compound 32).

EXAMPLE 33

2-(2,6-Dichloro-4-trifluoromethylphenyl)-5-methyl-2H-1,2,3-triazole-4-acetaldehyde was treated with diaminomaleonitrile in a similar manner to Example 1, to give 2-(2,6-dichloro-4-trifluoromethylphenyl)-4-[2-(2-amino-1,2-dicyanoethenylimino)ethyl]-5-methyl-2H-1,2,3-triazole, which was cyclised in a similar manner to Example 1a, to give 2-(2,6-dichloro-4-trifluoromethylphenyl)-4-[(4,5-dicyano-1H-imidazol-2-yl)methyl]-5-methyl-2H-1,2,3-triazole (Compound 33).

EXAMPLE 34

5-Amino-4-ethoxycarbonyl-1-(4-trifluoromethyl-2-nitrophenyl)-1H-pyrazole, was treated with bromoform in a similar manner to Example 11, to give ethyl 5-bromo-1-(4-trifluoromethyl-2-nitrophenyl)-1H-pyrazole-4-carboxylate. This was then reduced with zirconium borohydride to give [5-bromo-1-(4-trifluoromethyl-2nitrophenyl)-1H-pyrazol-4-yl]methanol, which was oxidised in a similar manner to that described in Example 4, to give 5-bromo-1-(4-trifluoromethyl-2-nitrophenyl)-1H-pyrazole-4-carboxaldehyde, which was converted, as described in Example 1, to 5-bromo-1-(4-trifluoromethyl-2-nitrophenyl)-4-[(2-amino-1,2-dicyanoethenylimino)-methyl]-1H-pyrazole, mp 195°–198°, which was cyclised to give 5-bromo-1-(4-trifluoromethyl-2-nitrophenyl)-4-(4,5-dicyano-1H-imidazol-2-yl)-1H-pyrazole, m.p. 86°–90°. (compound 34)

Intermediates and Starting Materials

A solution of sodium nitrite (45 g) in concentrated sulphuric acid (340 ml) was added to a solution of 2,6-dichloro-4-trifluoromethylaniline (140 g) in glacial acetic acid (550 ml) while maintaining the temperature below 25°. The mixture was stirred at room temperature for one hour, and was added quite rapidly to a stirred mixture of ethyl acetoacetate (80 g), sodium acetate (180 g), ethanol (300 ml) and ice-water (3 l ). After 1 hour, the brown solid was filtered and dried to give ethyl 2-(2,6-dichloro-4-trifluoromethylphenylhydrazono)-3-oxobutyrate.

This product (132 g) was added in portions to a stirred solution of hydroxylamine hydrochloride (25 g) and sodium acetate (48.5 g) in ethanol (1 l) and water (550 ml). The mixture was stirred at room temperature overnight and the yellow solid filtered and dried to give ethyl 3-(hydroxyimino)-2-(2,6-dichloro-4-trifluoromethylphenylhydrazono)butyrate.

This product (12 g) was stirred with acetic acid (60 ml) and acetic anhydride (90 ml) at room temperature for 3 hours. The mixture was poured into water and extracted with diethyl ether. The organic extracts were washed successively with 2N sodium hydroxide solution and brine, dried over magnesium sulphate and the solvent removed to yield ethyl 3-(acetyloxyimino)-2-(2,6-dichloro-4-trifluoromethylphenylhydrazono)butyrate.

A mixture of this product (6.4 g) and potassium carbonate in dry tetrahydrofuran was stirred at room temperature for 6 hours. The solvent was removed under reduced pressure and the residue taken up in ether. The ether extracts were washed with water, dried and evaporated to give 2-(2,6-dichloro-4-trifluoromethylphenyl)-4-ethoxycarbonyl-5-methyl-2H-1,2,3-triazole.

This product (5.4 g) was dissolved in dry tetrahydrofuran (50 ml) and added dropwise to a stirred solution of zirconium tetrachloride (4.3 9) and sodium borohydride (2.8 g) in dry tetrahydrofuran (100 ml). The mixture was stirred at room temperature overnight and then quenched with water (30 ml) and 2N hydrochloric acid (30 ml). The reaction mixture was extracted with diethyl ether and the organic extracts washed with water and dried over magnesium sulphate. Removal of the solvent at reduced pressure gave a thick oil which crystallised upon trituration with hexane to give crude [2-(2,6-dichloro-4-trifluoromethylphenyl)-5-methyl-2H-1,2,3-triazol-4-yl]-methanol.

In a similar manner,
a) 2-nitro-4-trifluoromethylaniline gave: [2-(2-nitro-4-trifluoromethylphenyl)-5-methyl-2H-1,2,3-triazol-4-yl]methanol, m.p. 69°-70°, b) 2,6-dichloro-4-trifluoromethylthioaniline gave: [2-(2,6-dichloro-4-trifluoromethylthiophenyl)-5-methyl-2H-1,2,3-triazol-4-yl]methanol, m/z 357 (M+,95%); 190 (100%), c) ethyl 4-methylthio-3-oxo-2-(2,6-dichloro-4-trifluoromethylphenylhydrazono)butyrate [formed from diazotised 2,6-dichloro-4-trifluoromethylaniline and ethyl 4-methylthio-3-oxobutyrate] gave:
 i) ethyl 3-(hydroxyimino)-4-methylthio-2-(2-6-dichloro-4-trifluoromethylphenylhydrazono)butyrate which, as a crude material was converted to:
 ii) 2-(2,6-dichloro-4-trifluoromethylphenyl)-4-ethoxycarbonyl-5-(methylthiomethyl)-2H-1,2,3-triazole, m.p. 68°-71°, which was converted to:
 iii) [2-(2,6-dichloro-4-trifluoromethylphenyl)-5-(methylthiomethyl)-2H-1,2,3-triazole-4-yl]methanol, used as crude material, d) ethyl 3-oxo-2-(2,6-dichloro-4-trifluoromethylphenylhydrazono)pentanoate, m.p 55°-65° [formed from reaction of diazotised 2,6-dichloro-4-trifluoromethylaniline and ethyl 3-oxopentanoate], gave crude [2-(2,6-dichloro-4-trifluoromethylphenyl)-5-ethyl-2H-1,2,3-triazole-4-yl]methanol, and e) ethyl 4,4,4-trifluoro-2-(hydroxyimino)-3-(2,6-dichloro-4-trifluoromethylphenylhydrazono)butyrate, [formed by condensation of 2,6-dichloro-4-trifluoromethylphenyl- hydrazine with ethyl 4,4,4-trifluoro-2-(hydroxyimino)-3-oxobutyrate in ethanol, containing a trace of sulphuric acid] gave on reaction with acetic acid/acetic anhydride/sodium acetate:
 i) 2-(2,6-dichloro-4-trifluoromethylphenyl)-4-ethoxycarbonyl-5-trifluoromethyl-2H-1,2,3-triazole, which was converted to
 (ii) [2-(2,6-dichloro-4-trifluoromethylphenyl)-5-trifluoromethyl-2H-1,2,3-triazole-4-yl]methanol, m.p. 78°-80°.

Ethyl 5-amino-1-(2,6-dichloro-4-trifluoromethylphenyl)-1H-pyrazole-4-carboxylate, was diazotised and treated with phosphorous acid to give ethyl 1-(2,6-dichloro-4-trifluoromethylphenyl)-1H-pyrazole-4-carboxylate, m.p. 70°-73°. This was reduced to [1-(2,6-dichloro-4-trifluoromethylphenyl)-1H-pyrazol-4-yl]methanol, m.p. 57°-59°

4,5-Dicyanoimidazole (23.6 g) was dissolved in sodium hydroxide solution (0.1N, 500 ml) with stirring and then bromine (36 ml) was added dropwise with stirring at room temperature. The mixture was stirred at room temperature overnight and the resulting solid was filtered, washed with water and dried to give 2-bromo-4,5-dicyanoimidazole m.p. 141°-144°. This compound (20 g) in dimethylformamide (100 ml) was added with stirring to a suspension of sodium hydride (80% dispersion in oil, 3.05 g) in dimethylformamide (100 ml) at room temperature. The mixture was cooled to 5° and chloromethyl 2-trimethylsilylethyl ether (18 ml) was added dropwise with stirring. This mixture was allowed to stand at room temperature overnight and was then poured into water and extracted with ethyl acetate. Evaporation of solvent gave an oil which was purified by column chromatography to give 1-(2-trimethylsilylethoxymethyl)-2-bromo-4,5-dicyano-1H-imidazole m.p.47°-52°.

In a similar manner, the following were obtained: 1-benzyl-2-bromo-4,5-dicyano-1H-imidazole, $n_D^{23}$: 1.601, and 1-allyl-2-bromo-4,5-dicyano-1H-imidazole, m.p. 85°-87°.

5-Chloro-1-(2,6-dichloro-4-trifluoromethylphenyl)-3-methyl-1H-pyrazole-4-carboxaldehyde (1.2 g) and sodium azide (0.3 g) were heated at 70° under a nitrogen atmosphere in dimethyl sulphoxide (15 ml) for 8 hours. The solvent was removed in vacuo and the residue redissolved in methanol (20 ml) containing piperidine (1 ml). This mixture was cooled to 15° while hydrogen sulphide gas was bubbled in slowly for 3 hours. The mixture was worked up to give 5-amino-1-(2,6-dichloro-4-trifluoromethylphenyl)-3-methyl-1H-pyrazole-4-carboxaldehyde, m.p. 169°-172°.

4-Trifluoromethyl-2-nitrophenylhydrazine (13.5 g) and ethyl 2-cyano-3-ethoxyacrylate (10.3 g) were heated under reflux in ethanol (300 ml) for 24 hours. The solvent was removed under reduced pressure and the resulting residue triturated with dichloromethane/hexane to give ethyl 2-cyano-3-(2-nitro-4-trifluoromethylphenylhydrazino)acrylate, m.p. 163°-164°.

This compound (6.3 g) was heated under reflux in ethanol (130 ml) containing a trace of p-toluenesulphonic acid for 60 hours. After removal of solvent and trituration of the residue with dichloromethane/hexane there was obtained 5-amino-4-ethoxycarbonyl-1-(4-trifluoromethyl-2-nitrophenyl)-1H-pyrazole, m.p. 118°-121°.

Diaminomaleonitrile (26.2 g) was added in portions to a solution containing cyanogen chloride (14.9 g) in tetrahydrofuran (200 ml). The mixture was then warmed to room temperature and finally heated under reflux for 1 hour. The resulting brown solid was collected by filtration and washed with a solution of sodium acetate. The remaining solid was dissolved in a sodium bicarbonate solution and treated with charcoal, filtered and acidified to give 2-amino-4,5-dicyanoimidazole, m.p. 276°–278°.

2-(2,6-Dichloro-4-trifluoromethylphenyl)-2$\underline{H}$-1,2,3-triazole-4-carboxaldehyde (15 g) and methyl methylthiomethyl sulphoxide (6 ml) were heated under reflux in tetrahydrofuran (100 ml) containing Triton B solution (6 ml; 40% in methanol) for 12 hours. The mixture was worked up to give 2-(2,6-dichloro-4-trifluoromethylphenyl)-4-(2-methylthio-2-methylsulphinylvinyl)-2$\underline{H}$-1,2,3-triazole, m.p. 122°–123°.

This product (1 g) was added as a solution in diethyl ether to a refluxing solution of lithium aluminium hydride (0.2 g) in diethyl ether (20 ml). After 20 minutes the reaction was quenched with water. Sodium hydroxide (25 ml; 2M) and ether were added and the mixture stirred for 15 minutes. The ether layer was separated dried and evaporated to dryness. The resulting solid was then recrystallised to give 2-(2,6-dichloro-4-trifluoromethylphenyl)-4-[2,2-di(methylthio)ethyl]-2$\underline{H}$-1,2,3-triazole, m.p. 97°–98°.

2,6-Dichloro-4-trifluoromethylphenylhydrazine (6.6 g) and 1-hexene-4,5-dione 4-oxime (3.4 g) were stirred in diethyl ether (200 ml) for 18 hours. The solvent was removed under reduced pressure to give 1-hexene-4,5-dione 5-(2,6-dichloro-4-trifluoromethylphenylhydrazone) 4-oxide, m.p. 86°–88°.

This product (1.6 g) was stirred in a mixture of acetic acid (10 ml) and acetic anhydride (20 ml) for 4 hours. Work up gave 1-hexene-4,5-dione 5-(2,6-dichloro-4-trifluoromethylphenylhydrazone) 4-(acetyloxide), m.p. 71°–73°.

This product (1 g) was heated under reflux with caesium carbonate (0.82 g) in tetrahydrofuran (30 ml) for 4 hours. The mixture was poured into water, acidified with dilute hydrochloric acid and extracted with ethyl acetate. Work up of the extract gave 2-(2,6-dichloro-4-trifluoromethylphenyl)-4-allyl-5-methyl-2$\underline{H}$-1,2,3-triazole, as an oil, m/z 335 (M+).

This product was oxidised to give crude 2-(2,6-dichloro-4-trifluoromethylphenyl)-5-methyl-2$\underline{H}$-1,2,3-triazole-4-acetaldehyde.

FORMULATION EXAMPLE

This example illustrates a typical concentrate that can be formulated from compounds of the invention.

| Suspension Concentrate | |
|---|---|
| Compound of the invention | 20 g/l |
| Sodium lignosulphonate | 5 g/l |
| Ethylene oxide/propylene oxide block copolymer | 5 g/l |
| Antifoam | 0.5 g/l |
| Water to | 1 l |

TEST EXAMPLE (1) Sheep blowfly (*Lucilia sericata*)

(a) Contact test 1 ml aliquots of acetone solutions or suspensions, containing test compound at various concentrations, were applied to cotton wool dental rolls (1 cm×2 cm), contained in glass vials 2 cm diameter×5 cm long. After drying, the treated materials were then impregnated with 1 ml of nutrient solution, infested with approximately 30 first instar larvae of sheep blow fly (*Lucilia sericata*), closed by a cotton wool plug and held at 25 for 24 hours. For the controls the mortality was <5% whereas compounds 1a, 1b, 1c, 1d, 1e, 1f, 1g, 2a, 3a, 3b, 4a, 4b, 4c, 4d, 4e, 4f, 5, 6b, 7, 8, 9a, 9b, 10, 11a, 11b, 13, 14a, 14b, 15, 16, 17, 18, 19, 21, 22a, 22b, 22c, 22d, 23, 26 and 27a had an $LC_{50}$ of less than 3000 ppm.

(b) systemic test 100 mg of test compound was dissolved in 0.2 ml dimethyl sulphoxide and diluted with corn oil to the desired concentration. Approx 0.25 ml doses were fed to male mice, using 5 mice for each dose. 4 hours after treatment the mice were killed with carbon dioxide and the upper parts of hind legs removed and skinned. These were placed individually into sample tubes which were infested with first instar larvae of sheep blow fly (*Lucilia sericata*), closed by a cotton wool plug and held at 25° or 24 hours. For the controls the mortality was <5% whereas compounds 1a, 1b, 1c, 1f, 2b, 3a, 3b, 4a, 9b, 11a, 22c, 27a and 27b had an $LC_{50}$ of less than 100 mg/kg of mouse.

(2) Ticks (*Boophilus microplus*)

(a) Larval test

Filter papers (9 cm diameter) were impregnated with 1 ml aliquots of acetone solutions or suspensions of test compound at various concentrations. The papers were allowed to dry and then folded into envelopes in which approximately 50 cattle tick larvae, (*Boophilus microplus*) were enclosed and held at 25° C. and >80% R.H. for 48 hours. The percentage mortality of tick larvae was then recorded and compared with controls. The controls gave less than 5% mortality whereas compound 1c had an $LD_{50}$ of less than 300 ppm.

(b) Female injection test

Test compounds were dissolved in a suitable solvent to a desired concentration. Using a microapplicator, 2 microlitres of the solution were injected into the blood filled stomach of a tick (*Boophilus microplus*). 5 replicate ticks were treated at each concentration and subsequently each tick is retained separately in partitioned petri dish held at 25° C. and >80% R.H., until mortality of ticks or fecundity and viability of eggs produced by survivors could be assessed. The percentage reduction in total reproductive capacity (i.e. the combined effects of adult mortality, reduced fecundity and mortality of eggs) was then recorded and compared with controls. The controls gave less than 5% reduction of reproductive capacity whereas compounds 4e, 6b and 28 gave at least 50% reduction of reproductive capacity at a concentration of 50 microgram/tick or less.

(3) Brown rice-hoppers (*Nilaparvata lugens* Stal)

Rice seedlings (*Oryzae sativa* L.) in the two leaf stage (about 10 per polystyrene pot of size 6.5×6.5 cm) were either untreated or dipped until dripping wet, with an aqueous preparation containing 0.1% of active material. After drying the sprayed leaves, a transparent cylinder was placed over each pot and through an opening, about 30 brown rice-hoppers (*Nilaparvata lugens*) in the 4–5 stage, anaesthetised with carbon dioxide, were introduced into each pot. After closing the opening with a fine mesh screen, the pots were kept for 2 days at 28°

C and 16 hours/day of light in the glasshouse, the amount of dead hoppers was determined. The percentage mortality was then estimated and the activity calculated using Abbott's method in comparison with the untreated controls. Compounds 1a and 4a showed an activity of 80% or more.

(4) Aphid (*Aphis fabae* Scoc.)

From the primary leaf of field beans (*Phaseolus vulgaris* nanus Aschers.), 24 mm diameter discs were cut. Some of these were treated with a 0.1% aqueous preparations of compounds of the invention and these along side untreated discs were placed on filter papers with the underside of the leaves turned upwards. After drying the test pieces, they were each infested with wingless stages of *Aphis fabae* (approx 100 per leaf piece). The experiment was replicated 3 times. The leaves were kept on wet filter papers for 2 days at 25° C. and 16 hours light per day. The percentage mortality was then estimated and the activity calculated using Abbott's method in comparison with the untreated controls. Compounds 1a, 1d, 4a, 6a, 6b, 7, 8 and 10 showed an activity of 80% or more.

(5) Two spotted mite (*Tetranychus urticae* Koch)

From the primary leaf of field beans (*Phaseolus vulgaris* nanus Aschers.) 14 mm diameter discs were cut. Some of these were treated with a 0.1% aqueous preparations of compounds of the invention and these along side untreated discs were placed on filter papers with the underside of the leaves turned upwards. After drying the test pieces, they were each infested with six adult female *Tetranychus urticae* and maintained for 3 days at 25° C. and 16 hours light per day. The experiment was replicated 4 times. Dead and alive adults were then counted and removed. Similarly the number of eggs laid were counted. After a further 7 days, the number of living larvae were counted, the activity calculated using Abbott's method in comparison with the untreated controls. Compounds 1a, 4a, 6a, 6b, 7 and 8 showed 80-100% activity against adults, eggs and larvae.

(6) House flies (*Musca domestica*)

Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies, (*Musca domestica*) and held at 22° C. for 48 hours. The percentage mortality of the insects was then recorded. Less than 5% mortality resulted in the control treatments whereas compounds 11b, 16, 17, 21, 22b and 24a had an $LC_{50}$ of 1000 mg/m² or less.

(7) Anthelmintic test (a) In vivo test

Groups of five mice were infected orally with 100 infective stage larvae (L3) of the murine gastrointestinal nematode *Heligmosomoides polygyrus*. After six days the mice were orally dosed with 50 μl of the test compound at the desired concentration in a carrier solution containing 1% wetter and 0.05% ethyl cellulose. A control group received carrier only. After 7 days the mice were killed and the small intestine examined for worm count. Compounds 1a, 1b, 4a, 14a, 22c and 27a at 100 mg/kg mouse body weight, gave >50% worm reduction compared with the controls.

(b) In vitro test

Adult worms of the parasitic nematode *Trichostrongylus colubriformis* were cultured in multi-well plates containing sterile culture medium and test compound at a concentration of 100 ppm. The cultures were maintained in a sterile carbon dioxide incubator at 37°, at a constant air/carbon dioxide ratio of 95:5 (v/v). After 5 days the control mortality was <5%, whereas compounds 1a, 1b, 1c, 1f, 2b, 3a, 3b, 4a, 4c, 4e, 4f, 5, 6b, 7, 10, 11a, 12, 13, 14a, 15, 22c, 22d, 27a and 28 had an $LC_{50}$ of less than 100 ppm.

(8) Root knot nematode, *Meloidogyne incognita*

10% of a powder preparation of the active ingredient prepared according to preparation No.I was mixed thoroughly with soil that had been strongly infested with the test nematode. After this the treated soil was put into a 0.5 liter fermenting tube, treated with cucumber seeds and cultivated at a soil temperature of 25° to 27° C. in a greenhouse. After a cultivation time of 25 to 28 days the cucumber roots were washed and inspected in a water bath for nematode attack (root knots) and the % level of activity of the active ingredients compared with a treated control was determined. When the nematode attack is fully controlled the level of activity is 100%. Compounds 1a, 1d and 4e had an $LC_{50}$ of less than 200 ppm.

We claim:

1. A compound of formula I

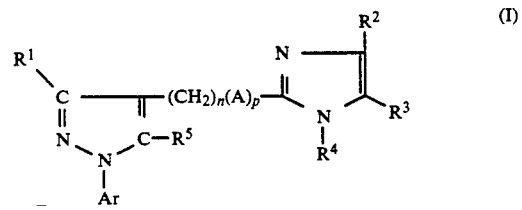

an agriculturally or veterinarily salts thereof, in which
Ar is 2,6-dichloro-4-trifluoromethylphenyl or 2-nitro-4-trifluoromethylphenyl A is $S(O)_m$, —CH=CH—, O or NH;

$R^1$ is hydrogen, optionally substituted alkyl, halogen or $R^{20}S(O)_q$;

$R^2$ and $R^3$ are hydrogen, alkyl, alkenyl or alkynyl, each of which is optionally substituted, aryl, cyano, halogen, nitro, $YR^{20}$, $S(O)_2NR^8R^9$, CHO, $NR^8R^9$ or $CYNR^8R^9$;

$R^4$ is hydrogen, optionally substituted alkyl, optionally substituted alkenyl, acyl or optionally substituted alkoxycarbonyl;

$R^5$ is hydrogen, alkyl, optionally substituted amino or halogen;

$R^8$ or $R^9$ are the same or different and are hydrogen, optionally substituted alkyl, acyl or aryl;

$R^{20}$ is optionally substituted alkyl;

Y is O or S;

m is 0, 1 or 2;

p is 0 or 2;

n is 0, 1 or 2; and q is 0, 1 or 2, and in which a) any alkyl, alkoxy and alkythio groups if of 1 to 4 carbon atoms;

b) any alkenyl or alkynyl groups is of 2 to 5 carbon atoms;
c) any substituted alkyl, alkoxy, alkylthio, alkenyl or alkynyl group is substituted by one or more of the same or different groups selected from halogen, $YR^{20}$, dihalocyclopropyl, cyano, nitro, optionally substituted amino, acyloxy and aryl;
d) any aryl group is phenyl, optionally substituted by halogen, alkyl, haloalkyl, alkoxy, haloalkoxy, alkylthio, haloalkylthio, haloalkylsulphonyl, cyano or nitro;
e) any acyl group is alkanoyl of 1 to 4 carbon atoms, or alkylsulphonyl or haloalkylsulphonyl; and
f) any optionally substituted amino groups is of formula $NR^8R^9$.

2. A compound according to claim 1, where $R^1$ is methyl.

3. A compound according to claim 1, where $R^4$ is hydrogen.

4. A compound according to claim 1, where at least one of $R^2$ and $R^3$ is cyano.

5. A compound according to claim 4, wherein $R^2$ and $R^3$ are both cyano.

6. A compound according to claim 5, where n and p are 0.

7. A compound according to claim 6, where Ar is 2,6-dichloro-4-trifluoromethylphenyl, $R^1$ is hydrogen, alkyl or alkylthio, $R^4$ is hydrogen and $R^5$ is alkyl or halogen.

8. A compound according to claim 7, where $R^1$ is methyl and $R^5$ is chlorine.

9. A compound according to claim 1, where n and p are 0.

10. A composition which comprises an effective insecticidal, acaricidal or animal endoparasiticidal amount of a compound as claimed in claim 1 in admixture with a pharmaceutically, agriculturally or veterinarily acceptable diluent or carrier.

11. A composition which comprises an effective insecticidal, acaricidal or animal endoparasiticidal amount of a compound as claimed in claim 4 in admixture with a pharmaceutically, agriculturally or veterinarily acceptable diluent or carrier.

12. A composition which comprises an effective insecticidal, acaricidal or animal endoparasiticidal amount of a compound as claimed in claim 7 in admixture with a pharmaceutically, agriculturally or veterinarily acceptable diluent or carrier.

13. A composition which comprises an effective insecticidal, acaricidal or animal endoparasiticidal amount of a compound as claimed in claim 8 in admixture with a pharmaceutically, agriculturally or veterinarily acceptable diluent or carrier.

14. A method of combating insects, acarids or animal endoparasites, at a locus or host for the same, infested or liable to be infested therewith, which comprises applying thereto an effective insecticidal, acaricidal or animal endoparasiticidal amount of a compound of formula I, as claimed in claim 1.

15. A method of combating insects, acarids or animal endoparasites, at a locus or host for the same, infested or liable to be infested therewith, which comprises applying thereto an effective insecticidal, acaricidal or animal endoparasiticidal amount of a compound of formula I, as claimed in claim 4.

16. A method of combating insects, acarids or animal endoparasites, at a locus or host for the same, infested or liable to be infested therewith, which comprises applying thereto an effective insecticidal, acaricidal or animal endoparasiticidal amount of a compound of formula I, as claimed in claim 7.

17. A method of combating insects, acarids or animal endoparasites, at a locus or host for the same, infested or liable to be infested therewith, which comprises applying thereto an effective insecticidal, acaricidal or animal endoparasiticidal amount of a compound of formula I, as claimed in claim 8.

* * * * *